United States Patent
Turner et al.

(10) Patent No.: US 9,500,716 B2
(45) Date of Patent: Nov. 22, 2016

(54) POWER MONITORING SYSTEMS AND METHODS

(71) Applicant: GRID20/20, Inc., Richmond, VA (US)

(72) Inventors: Randall Turner, Scarborough (CA); Michael Vandenberg, Erin (CA); Lan Xu, Toronto (CA); John Cecil Kuurstra, Mississauga (CA)

(73) Assignee: GRID 20/20, Inc., Richmond, VA (US)

( * ) Notice: Subject to any disclaimer, the term of this patent is extended or adjusted under 35 U.S.C. 154(b) by 101 days.

(21) Appl. No.: 14/231,576

(22) Filed: Mar. 31, 2014

(65) Prior Publication Data

US 2015/0276890 A1 Oct. 1, 2015

Related U.S. Application Data

(60) Provisional application No. 61/806,513, filed on Mar. 29, 2013.

(51) Int. Cl.

| | |
|---|---|
| *G01R 31/40* | (2014.01) |
| *G01R 21/00* | (2006.01) |
| *G01R 31/42* | (2006.01) |
| *G01R 31/00* | (2006.01) |
| *G01N 31/02* | (2006.01) |
| *G01N 27/42* | (2006.01) |
| *G01R 31/02* | (2006.01) |
| *G01R 1/073* | (2006.01) |
| *G01R 19/10* | (2006.01) |
| *G01R 31/28* | (2006.01) |

(52) U.S. Cl.
CPC ............... *G01R 31/40* (2013.01); *G01N 27/42* (2013.01); *G01N 31/02* (2013.01); *G01R 21/00* (2013.01); *G01R 31/002* (2013.01); *G01R 31/42* (2013.01); *G01R 1/073* (2013.01); *G01R 19/10* (2013.01); *G01R 31/2887* (2013.01)

(58) Field of Classification Search
CPC .... G01R 31/40; G01R 31/42; G01R 31/025; G01R 19/16538; G01R 19/165; G01R 31/002; G01R 1/073; G01R 19/10; G01R 31/2887; G01N 27/42; G01N 31/02
USPC ......... 324/71, 378, 403, 415, 425, 500, 537, 324/764.01
See application file for complete search history.

(56) References Cited

U.S. PATENT DOCUMENTS

| | | | |
|---|---|---|---|
| 6,507,184 B1 | 1/2003 | Elston | |
| 2005/0104567 A1 | 5/2005 | Beckwith | |
| 2008/0106425 A1* | 5/2008 | Deaver | G01R 19/16547 340/646 |
| 2008/0122642 A1* | 5/2008 | Radtke | G01R 19/16547 340/660 |
| 2009/0066317 A1 | 3/2009 | de Buda | |
| 2009/0289616 A1* | 11/2009 | Suozzo | G01R 31/024 324/66 |
| 2011/0075304 A1* | 3/2011 | Hamer | H02H 7/263 361/47 |
| 2012/0169323 A1 | 7/2012 | Ge et al. | |

(Continued)

*Primary Examiner* — Son Le
*Assistant Examiner* — Raul Rios Russo
(74) *Attorney, Agent, or Firm* — Ann I. Dennen

(57) ABSTRACT

The present disclosure is a system for monitoring power that has a unified polyphase distribution transformer monitoring (PDTM) device that interfaces with at least three electrical conductors electrically connected to a transformer. In addition, the PDTM device measures a current and a voltage of each of the three electrical conductors. Additionally, the system has logic that calculates values indicative of power corresponding to the transformer based upon the currents and the voltages measured and transmit data indicative of the calculated values.

14 Claims, 21 Drawing Sheets

(56) References Cited

U.S. PATENT DOCUMENTS

2013/0335061 A1* 12/2013 de Buda ................ G01R 21/06
    324/127

2013/0335062 A1* 12/2013 de Buda ................ G01R 21/00
    324/142

* cited by examiner

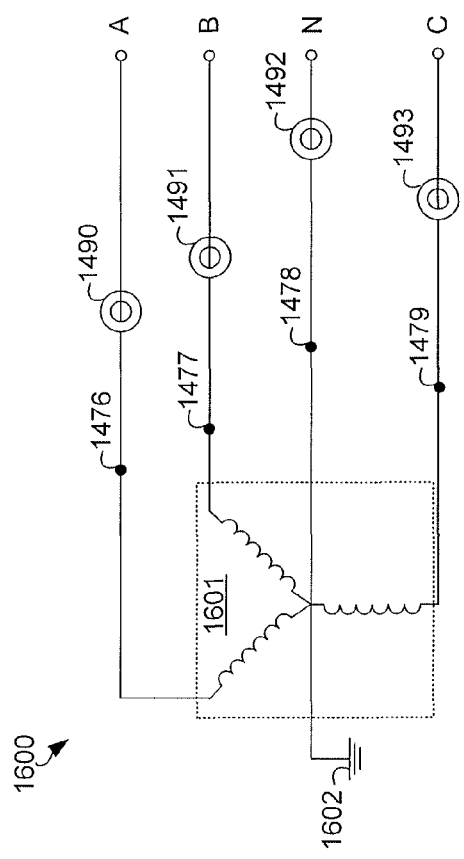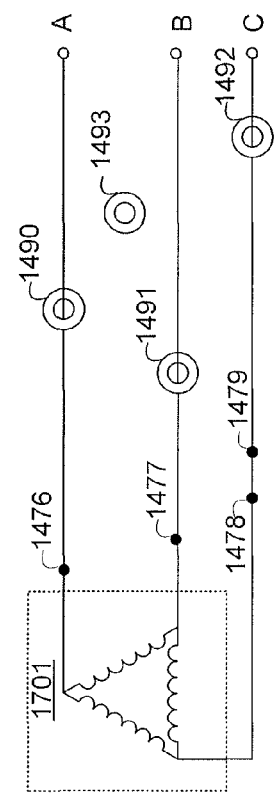
FIG. 16
FIG. 17

POWER MONITORING SYSTEMS AND METHODS

CROSS REFERENCE TO RELATED APPLICATIONS

This application claims priority to U.S. Provisional Application Ser. No. 61/806,513 entitled "Power Monitoring System and Method," filed Mar. 29, 2013, which is incorporated herein by reference in its entirety.

BACKGROUND

Power is generated, transmitted, and distributed to a plurality of endpoints, such as for example, customer or consumer premises (hereinafter referred to as "consumer premises"). Consumer premises may include multiple-family residences (e.g., apartment buildings, retirement homes), single-family residences, office buildings, event complexes (e.g., coliseums or multi-purpose indoor arenas, hotels, sports complexes), shopping complexes, or any other type of building or area to which power is delivered.

The power delivered to the consumer premises is typically generated at a power station. A power station is any type of facility that generates power by converting mechanical power of a generator into electrical power. Energy to operate the generator may be derived from a number of different types of energy sources, including fossil fuels (e.g., coal, oil, natural gas), nuclear, solar, wind, wave, or hydroelectric. Further, the power station typically generates alternating current (AC) power.

The AC power generated at the power station is typically increased (the voltage is "stepped up") and transmitted via transmission lines typically to one or more transmission substations. The transmission substations are interconnected with a plurality of distribution substations to which the transmission substations transmit the AC power. The distribution substations typically decrease the voltage of the AC power received (the voltage is "stepped down") and transmit the reduced voltage AC power to distribution transformers that are electrically connected to a plurality of consumer premises. Thus, the reduced voltage AC power is delivered to a plurality of consumer premises. Such a web or network of interconnected power components, transmission lines, and distribution lines is often times referred to as a power grid.

Throughout the power grid, measureable power is generated, transmitted, and distributed. In this regard, at particular midpoints or endpoints throughout the grid, measurements of power received and/or distributed may indicate information related to the power grid. For example, if power distributed at the endpoints on the grid is considerably less than the power received at, for example, distribution transformers, then there may be a system issue that is impeding delivery of power or power may be being diverted through malice. Such power data collection at any of the described points in the power grid and analysis of such data may further aid power suppliers in generating, transmitting, and distributing power to consumer premises.

SUMMARY

The present disclosure is a system for monitoring power that has a polyphase distribution transformer monitoring (PDTM) device that interfaces with at least three electrical conductors electrically connected to a transformer. The PDTM device further measures a current and a voltage of each of the three electrical conductors. The system further has logic that calculates values indicative of power corresponding to the transformer based upon the current and the voltage measured and transmit data indicative of the calculated values.

BRIEF DESCRIPTION OF THE DRAWINGS

The present disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 16 is a diagram depicting a method of monitoring power with a PDTM of FIG. 14 in accordance with the system such as is depicted in FIG. 1 for a wye transformer configuration.

FIG. 17 is a diagram depicting a method of monitoring power with a PDTM of FIG. 14 in accordance with the system such as is depicted in FIG. 1 for a Delta transformer configuration.

DETAILED DESCRIPTION

Figure 1:
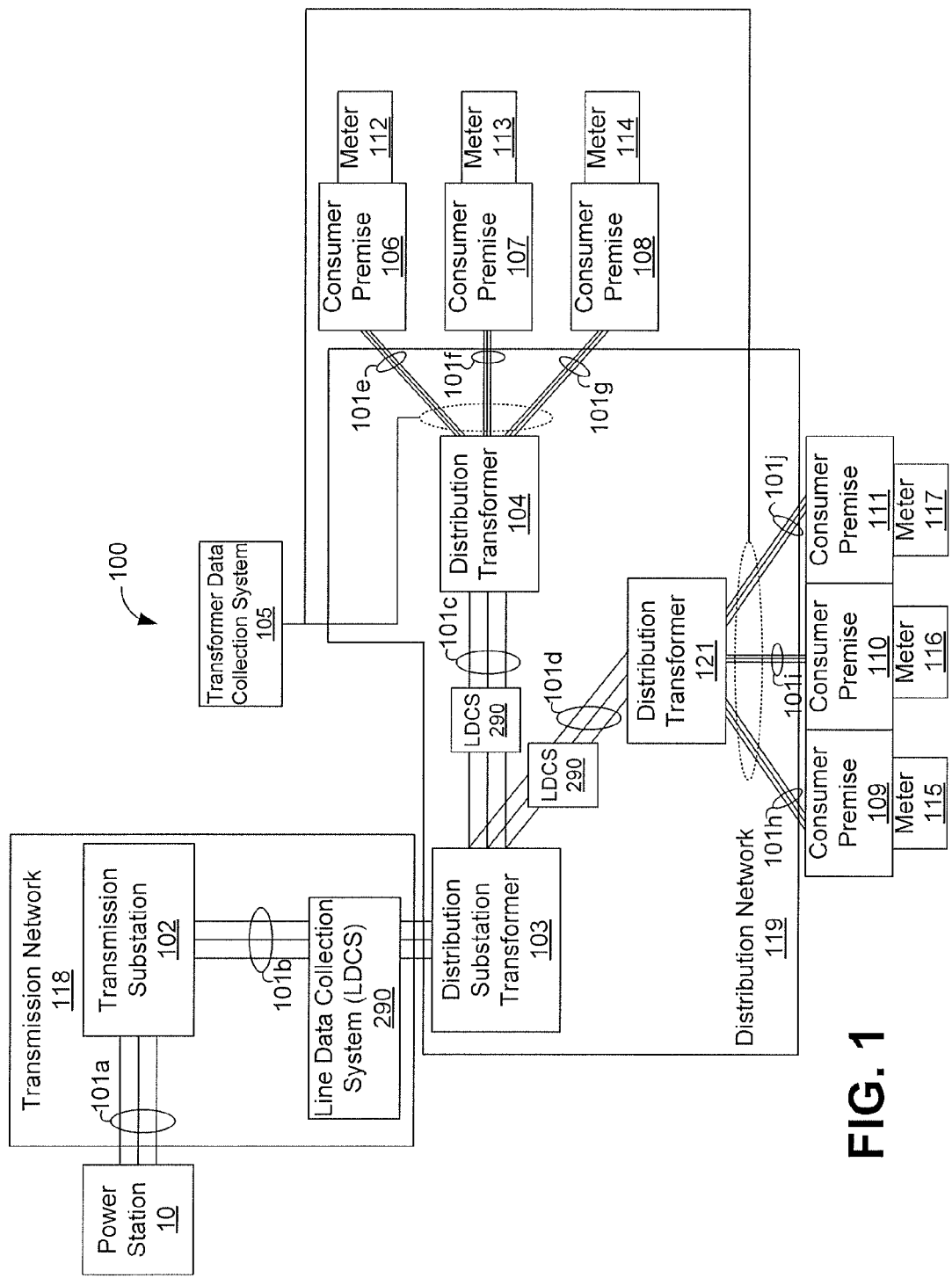
FIG. 1 is a diagram depicting an exemplary power transmission and distribution system in accordance with an embodiment of the present disclosure.

FIG. 1 is a block diagram illustrating a power transmission and distribution system 100 for delivering electrical power to one or more consumer premises 106-111. The one or more consumer premises 106-111 may be business consumer premises, residential consumer premises, or any other type of consumer premise. A consumer premise is any structure or area to which power is delivered.

The power transmission and distribution system 100 comprises at least one transmission network 118, at least one distribution network 119, and the consumer premises 106-111 (described hereinabove) interconnected via a plurality of power lines 101a-101j.

In this regard, the power transmission and distribution system 100 is an electric "grid" for delivering electricity generated by a power station 10 to the one or more consumer premises 106-111 via the transmission network 118 and the distribution network 119.

Note that the power lines 101a and 101b are exemplary transmission lines, while power lines 101c, 101d, are exemplary distribution lines. In one embodiment, the transmission lines 101a and 101b transmit electricity at high voltage (110 kV or above) and often via overhead power lines. At distribution transformers, the AC power is transmitted over the distribution lines at lower voltage (e.g., 25 kV or less). Note that in such an embodiment, the power transmission described uses three-phase alternating current (AC). However, other types of power and/or power transmission may be used in other embodiments.

The transmission network 118 comprises one or more transmission substation 102 (only one is shown for simplicity). The power station 10 is electrically coupled to the transmission substation 102 via the power lines 101a, and the transmission substation 102 is electrically connected to the distribution network 119 via the power lines 101b. As described hereinabove, the power station 10 (transformers not shown located at the power station 10) increases the voltage of the power generated prior to transmission over the transmission lines 101a to the transmission substation 102. Note that three wires are shown making up the power lines 101a indicating that the power transmitted to the transmission substation 102 is three-phase AC power. However, other types of power may be transmitted in other embodiments.

In this regard, at the power station 10, electricity is generated, and the voltage level of the generated electricity is "stepped up," i.e., the voltage of the generated power is increased to high voltage (e.g., 110 kV or greater), to decrease the amount of losses that may occur during transmission of the generated electricity through the transmission network 118.

Note that the transmission network 118 depicted in FIG. 1 comprises only two sets of transmission lines 101a and 101b (three lines each for three-phase power transmissions as indicated hereinabove) and one transmission substation 102. The configuration of FIG. 1 is merely an exemplary configuration. The transmission network 118 may comprise additional transmission substations interconnected via a plurality of additional transmission lines. The configuration of the transmission network 118 may depend upon the distance that the voltage-increased electricity may need to travel to reach the desired distribution network 119.

The distribution network 119 transmits electricity from the transmission network 118 to the consumer premises 106-111. In this regard, the distribution network 119 comprises a distribution substation transformer 103 and one or more distribution transformers 104 and 121. Note that the configuration shown in FIG. 1 comprising the distribution substation transformer 103 and two distribution transformers 104 and 121 and showing the distribution substation transformer 103 physically separated from the two distribution transformers 104 and 121 is an exemplary configuration. Other configurations are possible in other embodiments.

As an example, the distribution substation transformer 103 and the distribution transformer 104 may be housed or combined together in other configurations of the distribution network 119 (as well as distribution substation transformer 103 and distribution transformer 121). In addition, one or more transformers may be used to condition the electricity, i.e., transform the voltage of the electricity, to an acceptable voltage level for delivery to the consumer premises 106-111. The distribution substation transformer 103 and the distribution transformer 104 may "step down," i.e., decrease the voltage of the electricity received from the transmission network 118, before the distribution substation transformer 103 and the distribution transformers 104, 121 transmit the electricity to its intended destinations, e.g., the consumer premises 106-111.

As described hereinabove, in operation the power station 10 is electrically coupled to the transmission substation 102 via the power lines 101a. The power station 10 generates electricity and transmits the generated electricity via the power lines 101a to the transmission substation 102. Prior to transmission, the power station 10 increases the voltage of the electricity so that it may be transmitted over greater distances efficiently without loss that affects the quality of the electricity delivered. As further indicated hereinabove, the voltage of the electricity may need to be increased in order to minimize energy losses as the electricity is being transmitted on the power lines 101b. The transmission substation 102 forwards the electricity to the distribution substation transformer 103 of the distribution network 119.

When the electricity is received, the distribution substation transformer 103 decreases the voltage of the electricity to a range that is useable by the distribution transformers 104, 121. Likewise, the distribution transformers 104, 121 may further decrease the voltage of the electricity received to a range that is useable by the respective electrical systems (not shown) of the consumer premises 106-111.

In one embodiment of the present disclosure, the distribution transformers 104, 121 are electrically coupled to a distribution transformer data collection system 105. The distribution transformer data collection system 105 of the present disclosure comprises one or more electrical devices (the number of devices may be determined based upon the number of transformers being monitored) (not shown) that measure operational data via one or more electrical interfaces with the distribution transformers 104, 121. Exemplary operational data includes data related to electricity that is being delivered to or transmitted from the distribution transformers 104, 121, e.g., power measurements, energy measurements, voltage measurements, current measurements, etc. In addition, the distribution transformer data collection system 105 may collect operational data related to the environment in which the distribution transformers 104, 121 are situated, e.g., operating temperature of the distribution transformers 104, 121.

In accordance with one embodiment of the present disclosure, the distribution transformer data collection system 105 electrically interfaces with power lines 101e-101j (e.g., a set of three power lines delivering power to consumer premises 106-111, if the power is three-phase). Thus, the distribution transformer data collection system 105 collects the data, which represents the amount of electricity (i.e., power being used) that is being delivered to the consumer premises 106-111. In another embodiment, the distribution transformer data collection system 105 may electrically interface with the power lines 101c-101d (i.e., the power lines delivering receiving power from the transmission network 118).

Furthermore, each consumer premise 106-111 comprises an electrical system (not shown) for delivering electricity received from the distribution transformers 104, 121 to one or more electrical ports (not shown) of the consumer premise 106-111. Note that the electrical ports may be internal or external ports.

The electrical system of each consumer premise 106-111 interfaces with a corresponding consumer premise's electrical meter 112-117, respectively. Each electrical meter 112-117 measures the amount of electricity consumed by the consumer premises' electrical system to which it is coupled. In order to charge a customer who is responsible for the consumer premise, a power company (e.g., a utility company or a metering company) retrieves data indicative of the measurements made by the electrical meters 112-117 and uses such measurements to determine the consumer's invoice dollar amount representative of how much electricity has been consumed at the consumer premise 106-111. Notably, readings taken from the meters 112-117 reflect the actual amount of power consumed by the respective consumer premise electrical system. Thus, in one embodiment of the present disclosure, the meters 112-117 store data indicative of the power consumed by the consumers.

During operation, the meters 112-117 may be queried using any number of methods in order to retrieve and store data indicative of the amount of power being consumed by the meter's respective consumer premise electrical system. In this regard, utility personnel may physically go to the consumer premises 106-111 and read the consumer premise's respective meter 112-117. In such a scenario, the personnel may enter data indicative of the readings into an electronic system, e.g., a hand-held device, a personal computer (PC), or a laptop computer. Periodically, the data entered may be transmitted to an analysis repository. Additionally, meter data retrieval may be electronic and automated. For example, the meters 112-117 may be communicatively coupled to a network (not shown), e.g., a wireless network, and periodically the meters 112-117 may automatically transmit data to a repository, described herein with reference to FIG. 2A.

As will be described further herein, meter data (not shown) (i.e., data indicative of readings taken by the meters 112-117) and transformer data (not shown) (i.e., data indicative of readings taken by the transformer monitoring data collection system 105) may be stored, compared, and analyzed in order to determine whether particular events have occurred, for example, whether electricity theft is occurring or has occurred between the distribution transformers 104, 121 and the consumer premises 106-111 or to determine whether power usage trends indicate a need or necessity for additional power supply equipment. In this regard, with respect to the theft analysis, if the amount of electricity being received at the distribution transformers 104, 121 is much greater than the cumulative (or aggregate) total of the electricity that is being delivered to the consumer premises 106-117, then there is a possibility that an offender may be stealing electricity from the utility providing the power.

In another embodiment, power usage data is compiled over time. The compilation of the power usage data may be used in a number of different ways. For example, it may be predetermined that a particular power usage signature, e.g., power usage which can be illustrated as a graphed footprint over a period of time, indicates nefarious activity. Such is described further herein.

In one embodiment, the power transmission and distribution system 100 further comprises a line data collection system (LDCS) 290. The LDCS 290 collects line data from the transmission lines 101b-101d. The line data is data indicative of power/electricity measured. Such data may be compared, for example, to meter data (collected at consumer premises 106-111 described further herein) and/or the transformer data (collected at the distribution transformers 104, 121 described further herein) in order to determine losses of electricity along the power grid, electricity usage, power need, or power consumption metrics of the power grid. In one embodiment, data collected may be used to determine whether electricity theft is occurring or has occurred between a transmission substation and a distribution substation or a distribution substation and a distribution transformer (i.e., the distribution transformer that transmits power to the consumer premise). Note that the LDCS 290 is coupled to the transmission lines 101b, 101c, and 101d, respectively, thus coupling to medium voltage (MV) power lines. The LDCS 290 measures and collects operational data, as described hereinabove. In one embodiment, the LDCS may transmit operational data, such as, for example, power, energy, voltage, and/or current, related to the MV power lines 101b, 101c, and 101d.

Figure 2A:
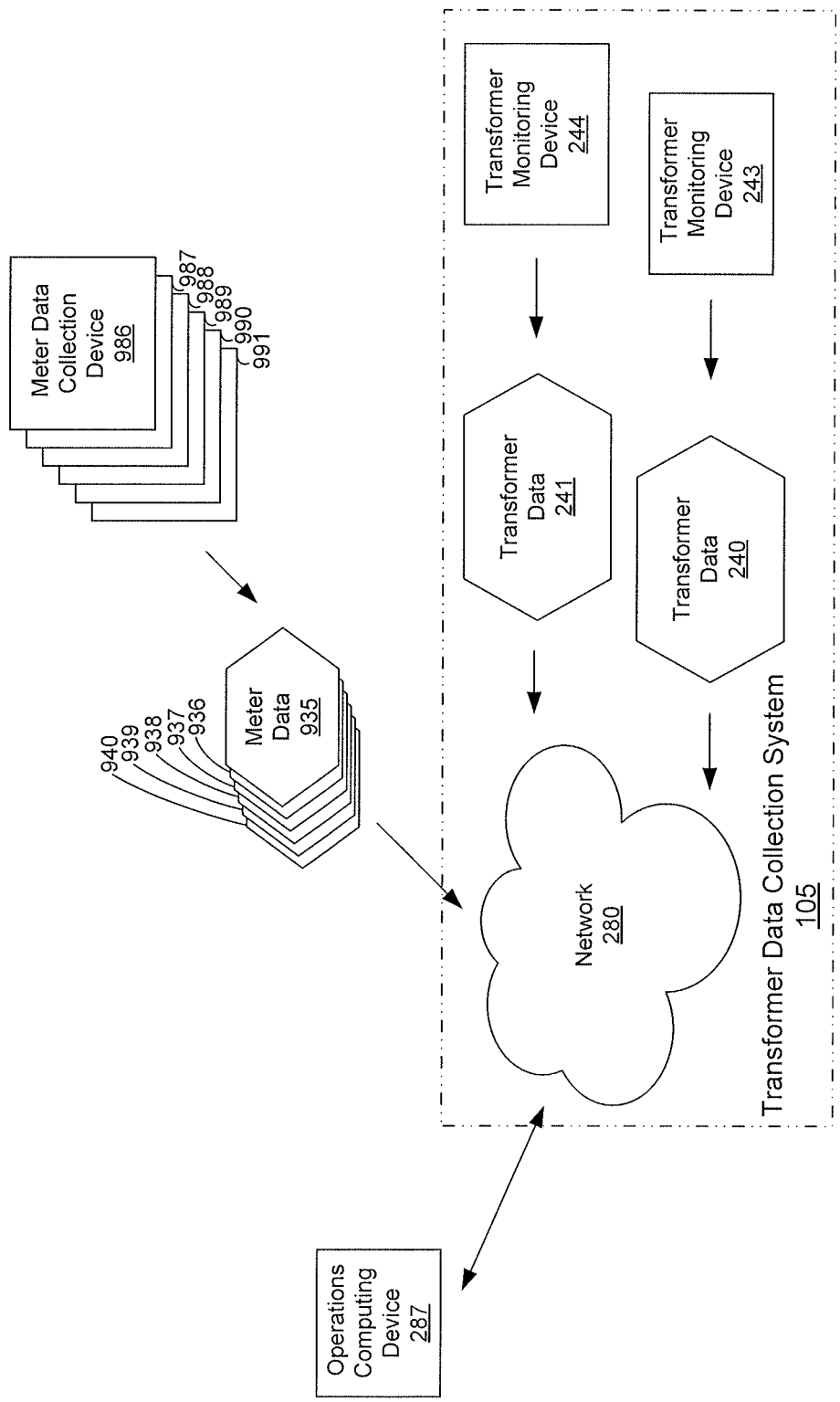
FIG. 2A is a diagram depicting a transformer and meter power usage data collection system in accordance with an embodiment of the present disclosure.

FIG. 2A depicts the transformer data collection system 105 in accordance with an embodiment of the present disclosure and a plurality of meter data collection devices 986-991. The transformer data collection system 105 comprises one or more transformer monitoring devices 243, 244 (FIG. 1). Note that only two transformer monitoring devices 243, 244 are shown in FIG. 2A but additional transformer monitoring devices may be used in other embodiments, one or a plurality transformer monitoring devices for each distribution transformer 104, 121 (FIG. 1) being monitored, which is described in more detail herein.

Notably, in one embodiment of the present disclosure, the transformer monitoring devices 243, 244 are coupled to secondary side of the distribution transformers, 104, 121 respectively. Thus, measurements taken by the transformer monitoring devices 243, 244 are taken, in effect, at the distribution transformers 104, 121 between the distribution transformers 243, 244 and the consumer premises 106-111 (FIG. 1).

Additionally, the transformer monitoring devices 243, 244, the meter data collection devices 986-991, and an operations computing device 287 may communicate via a network 280. The network 280 may be any type of network over which devices may transmit data, including, but not limited to, a wireless network, a wide area network, a large area network, or any type of network known in the art or future-developed.

In another embodiment, the meter data 935-940 and the transformer data 240, 241, may be transmitted via a direct connection to the operations computing device 287 or manually transferred to the operations computing device 287. As an example, the meter data collection devices 986-991 may be directly connected to the operations computing device 287 via a direction connection, such as for example a T-carrier 1 (T1) line. Also, the meter data 935-940 may be collected on by a portable electronic device (not shown) that is then connected to the operations computing device 287 for transfer of the meter data collected to the operations computing device 287. In addition, meter data 935-940 may be collected manually through visual inspection by utility personnel and provided to the operations computing device 287 in a particular format, e.g., comma separated values (CSV).

Note that in other embodiments of the present disclosure, the meter data collection devices 986-991 may be the meters 112-117 (FIG. 1) themselves, and the meters 112-117 may be equipped with network communication equipment (not shown) and logic (not shown) configured to retrieve readings, store readings, and transmit readings taken by the meters 112-117 to the operations computing device 287.

The transformer monitoring devices 243, 244 are electrically coupled to the distribution transformers 104, 121, respectively. In one embodiment, the devices 243, 244 are electrically coupled to the distribution transformers 104, 121, respectively, on a secondary side of the distribution transformers 104, 121.

The transformer monitoring devices 243, 244 each comprise one or more sensors (not shown) that interface with one or more power lines (not shown) connecting the distribution transformers 104, 121 to the consumer premises 106-111 (FIG. 1). Thus, the one or more sensors of the transformer monitoring devices 243, 244 senses electrical characteristics, e.g., voltage and/or current, present in the power lines as power is delivered to the consumer premises 106-111 through the power lines 101e-101f. Periodically, the transformer monitoring devices 243, 244 sense such electrical characteristics, translate the sensed characteristics into transformer data 240, 241 indicative of electrical characteristics, such as, for example power, and transmit transformer data 240, 241 to the operations computing device 287 via the network 280. Upon receipt, the operations computing device 287 stores the transformer data 240, 241 received.

Note that there is a transformer monitoring device depicted for each distribution transformer in the exemplary system, i.e., transformer monitoring device 243 for monitoring transformer 104 (FIG. 1) and transformer monitoring device 244 for monitoring transformer 121 (FIG. 1). There may be additional transformer monitoring devices for monitoring additional transformers in other embodiments.

The meter data collection devices 986-991 are communicatively coupled to the network 280. During operation, each meter data collection device 986-991 senses electrical characteristics of the electricity, e.g., voltage and/or current, that is transmitted by the distribution transformers 104, 121. Each meter data collection device 986-991 translates the sensed characteristics into meter data 935-940, respectively. The meter data 935-940 is data indicative of electrical characteristics, such as, for example power consumed in addition to specific voltage and/or current measurements. Further, each meter data collection device 986-991 transmits the meter data 935-940, respectively, to the operations computing device 287 via the network 280. Upon receipt, the operations computing device 287 stores the meter data 935-940 received from the meter data collection devices 986-991 indexed (or keyed) with a unique identifier corresponding to the meter data collection device 986-991 that transmits the meter data 935-940.

In one embodiment, each meter data collection device 986-991 may comprise Automatic Meter Reading (AMR) technology, i.e., logic (not shown) and/or hardware, or Automatic Metering Infrastructure (AMI) technology, e.g., logic (not shown) and/or hardware for collecting and transmitting data to a central repository, (or more central repositories,) e.g., the operations computing device 287.

In such an embodiment, the AMR technology and/or AMI technology of each device 986-991 collects data indicative of electricity consumption by its respective consumer premise power system and various other diagnostics information. The meter logic of each meter data collection device 986-991 transmits the data to the operations computing device 287 via the network 280, as described hereinabove. Note that the AMR technology implementation may include hardware such as, for example, handheld devices, mobile devices and network devices based on telephony platforms (wired and wireless), radio frequency (RF), or power line communications (PLC).

Upon receipt, the operations computing device 287 compares aggregate meter data of those meters corresponding to a single transformer with the transformer data 240, 241 received from the transformer that provided the transformer data 240, 241.

Thus, assume that meter data collection devices 986-988 are coupled to meters 112-114 (FIG. 1) and transmit meter data 935-937, respectively, and distribution transformer 104 is coupled to transformer monitoring device 243. In such a scenario, the meters 112-114 meter electricity provided by the distribution transformer 104 and consumed by the electrical system of the respective consumer premise 106-108. Therefore, the operations computing device 287 aggregates (e.g., sums) data contained in meter data 935-937 (e.g., power usage recorded by each meter 112-114) and compares the aggregate with the transformer data 240 provided by transformer monitoring device 243.

If the operations computing device 287 determines that the quantity of power that is being delivered to the consumer premises 106-108 connected to the distribution transformer 104 is substantially less than the quantity of power that is being transmitted to the distribution transformer 104, the operations computing device 287 may determine that power (or electricity) theft is occurring between the distribution transformer 104 and the consumer premises 106-108 to which the distribution transformer 104, is connected.

In one embodiment, the operations computing device 287 may store data indicating theft of electricity. In another embodiment, the operations computing device 287 may be monitored by a user (not shown), and the operations computing device 287 may initiate a visual or audible warning that power (or electricity) theft is occurring. This process is described further herein.

In one embodiment, the operations computing device 287 identifies, stores, and analyzes meter data 935-940 based on a particular unique identifier associated with the meter 112-117 to which the meter data collection devices 986-991 are coupled. Further, the operations computing device 287 identifies, stores, and analyzes transformer data 240, 241 based on a unique identifier associated with the distribution transformers 104, 121 that transmitted the transformer data 240, 241 to the operations computing device 287.

Thus, in one embodiment, prior to transmitting data to the operations computing device 287, both the meter data collection devices 986-991 and the transformer monitoring devices 243, 244 are populated internally with a unique identifier (i.e., a unique identifier identifying the meter data collection device 986-991 and a unique identifier identifying the transformer monitoring device 243, 244). Further, each meter data collection device 986-991 may be populated with the unique identifier of the transformer 104, 121 to which the meter data collection device 986-991 is connected.

In such an embodiment, when the meter data collection device 986-991 transmits the meter data 935-940 to the operations computing device 287, the operations computing device 287 can determine which distribution transformer 104 or 121 services the particular consumer premises 106-111. As an example, during setup of a portion of the grid (i.e., power transmission and distribution system 100) that comprises the distribution transformers 104, 121 and the meters 112-117, the operations computing device 287 may receive set up data from the distribution transformers 104, 121 and the meter data collection devices 986-991 identifying the device from which it was sent and a unique identifier identifying the component to which the meter data collection device 986-990 is connected.

Figure 2B:
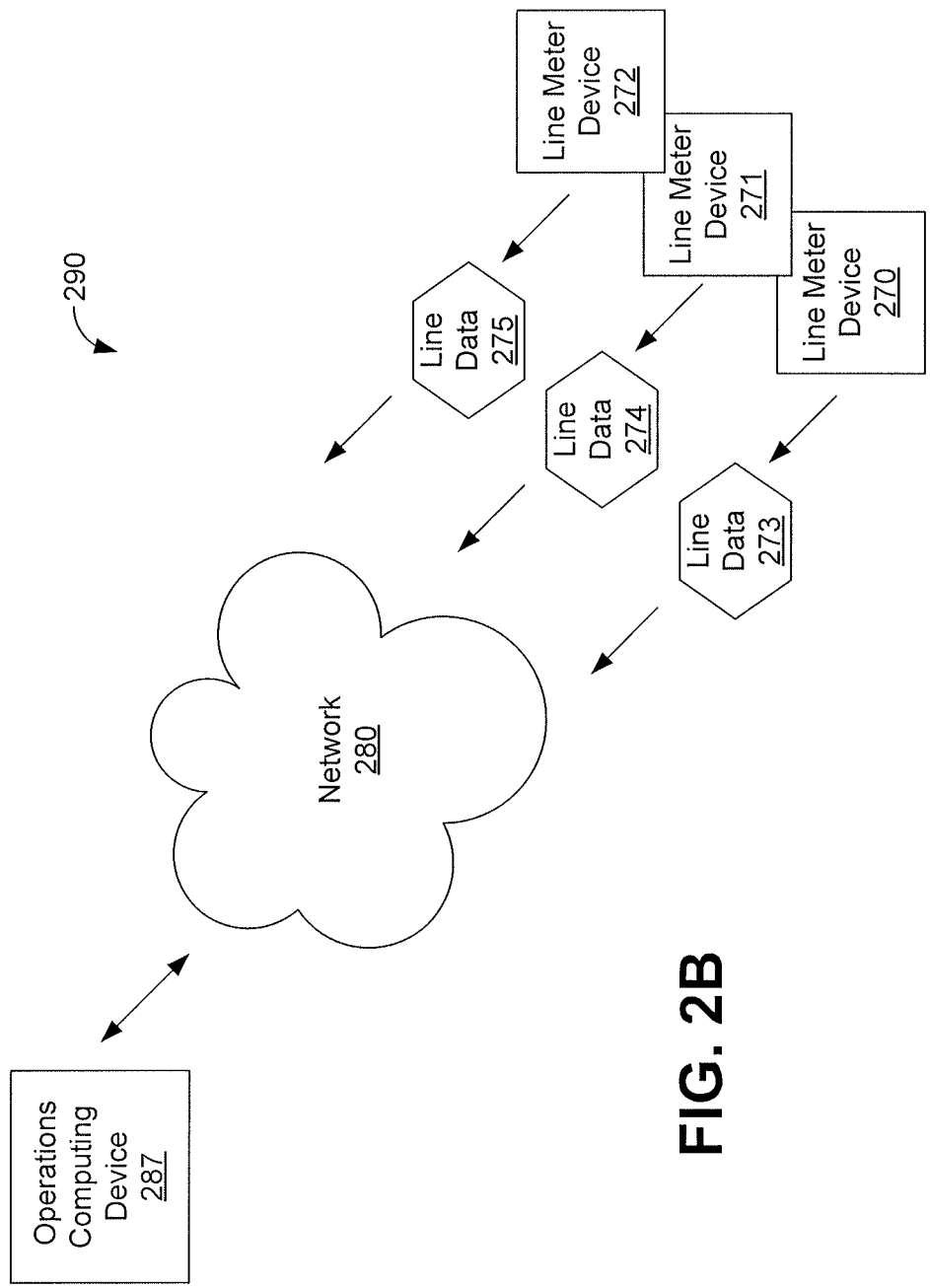
FIG. 2B is a diagram depicting a line power usage data collection system in accordance with an embodiment of the present disclosure.

FIG. 2B depicts the line data collection system 290 in accordance with an embodiment of the present disclosure. The line data collection system 290 comprises a plurality of line monitoring devices 270-272 and the operations computing device 287. Each line monitoring device 270-272 communicates with the operations computing device 287 via the network 280.

With reference to FIG. 1, the line monitoring devices 270-272 are electrically coupled to the transmission lines 101*b*, 101*c*, and 101*d*, respectively. In one embodiment, each line monitoring device 270-272 comprises one or more sensors (not shown) that interface with the transmission lines 101*b*, 101*c*, and 101*d* connecting the transmission substation 102 downstream to the distribution substation transformer 103 or connecting the distribution substation transformer 103 downstream to the distribution transformers 104, 121.

The one or more sensors of the line monitoring devices 270-272 sense electrical characteristics, e.g., voltage and/or current, present as current flows through transmission lines 101*b*, 101*c*, and 101*d*, respectively. Periodically, each line monitoring device 270-272 senses such electrical characteristics, translates the sensed characteristics into line data 273-275, respectively, indicative of such characteristics, and transmits the line data 273-275 to the operations computing device 287 via the network 280. Upon receipt, the operations computing device 287 stores the line data 273-275 received from the line monitoring devices 270-272.

Figure 3:
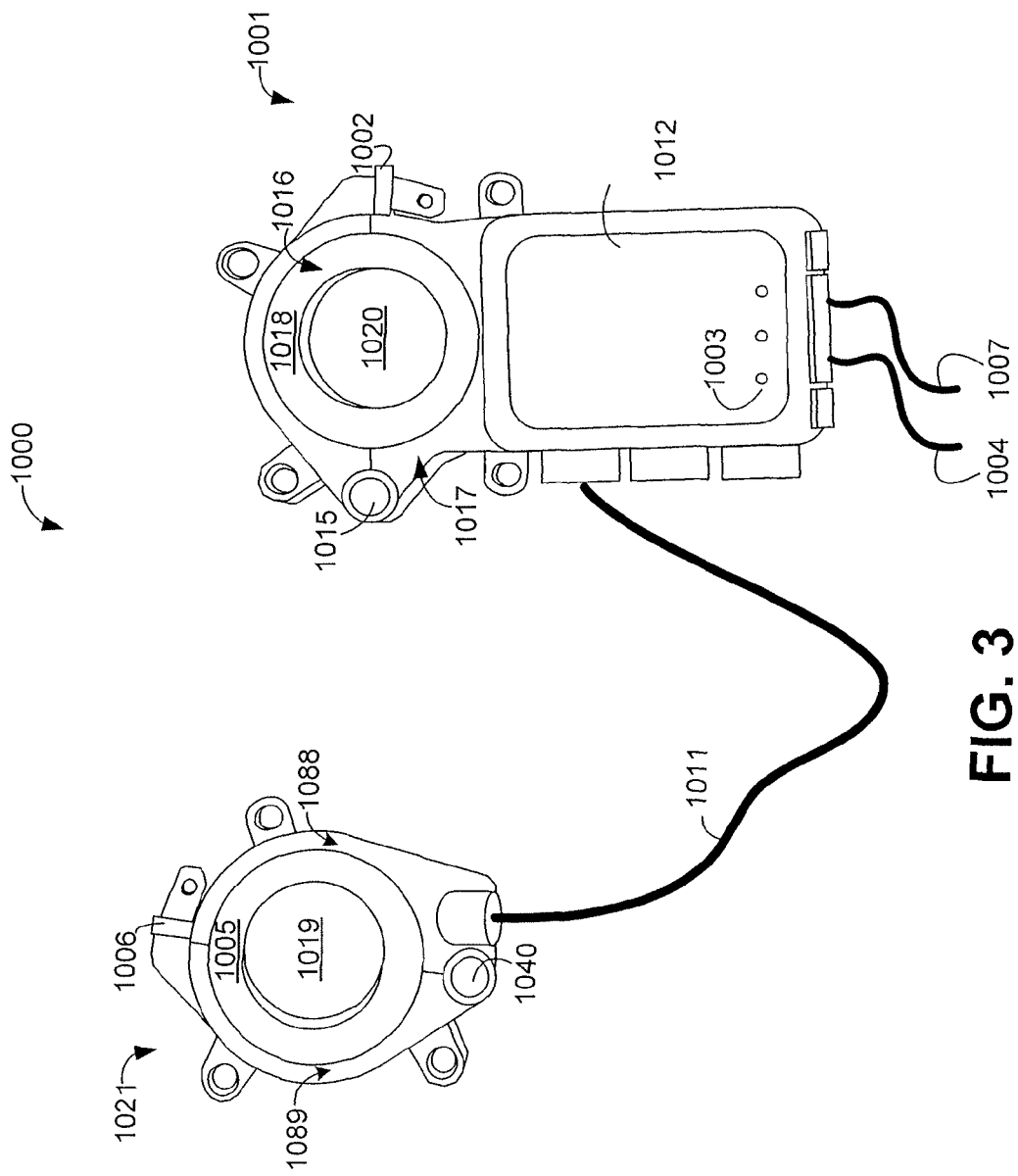
FIG. 3 is a drawing of a general purpose transformer monitoring device, such as is depicted by FIG. 2A.

FIG. 3 depicts an embodiment of a general purpose transformer monitoring device 1000 that may be used as the transformer monitoring devices 243, 244 depicted in FIG. 2A and/or line monitoring devices 270-272 (FIG. 2B). The transformer monitoring device 1000 may be installed on conductor cables (not shown) and used to collect data indicative of voltage and/or current from the conductor cables to which it is coupled.

The general purpose transformer monitoring device 1000 comprises a satellite unit 1021 that is electrically coupled to a main unit 1001. In one embodiment, the satellite unit 1021 is coupled via a cable 1011. However, the satellite unit 1021 may be coupled other ways in other embodiments, e.g., wirelessly. The general purpose transformer monitoring device 1000 may be used in a number of different methods in order to collect voltage and/or current data (i.e., transformer data 240, 241 (FIG. 2A) from the distribution transformers 104, 121 (FIG. 1) and from the power lines 101*b*-101*j*.

In order to collect voltage and/or current data, the satellite unit 1021 and/or the main unit 1001 is installed around a conductor cable or connectors of conductor cables (also known as a "bushing").

In this regard, the satellite unit 1021 of the general purpose transformer monitoring device 1000 comprises two sections 1088 and 1089 that are hingedly coupled at hinge 1040. When installed and in a closed position (as shown in FIG. 3), the sections 1088 and 1089 connect together via a latch 1006 and the conductor cable runs through an opening 1019 formed by coupling the sections 1088 and 1089.

The satellite unit 1021 further comprises a sensing unit housing 1005 that houses a current detection device (not shown) for sensing current flowing through the conductor cable around which the sections 1088 and 1089 are installed. In one embodiment, the current detection device comprises an implementation of one or more coreless current sensor as described in U.S. Pat. No. 7,940,039, which is incorporated herein by reference.

The main unit 1001 comprises sections 1016 and 1017 that are hingedly coupled at hinge 1015. When installed and in a closed position (as shown in FIG. 3), the sections 1016 and 1017 connect together via a latch 1002 and a conductor cable runs through an opening 1020 formed by coupling the sections 1016 and 1017.

The main unit 1001 comprises a sensing unit housing section 1018 that houses a current detection device (not shown) for sensing current flowing through the conductor cable around which the sections 1016 and 1017 are installed. As described hereinabove with respect to the satellite unit 1021, the current detection device comprises an implementation of one or more Ragowski coils as described in U.S. Pat. No. 7,940,039, which is incorporated herein by reference.

Unlike the satellite unit 1021, the main unit section 1017 comprises an extended boxlike housing section 1012. Within the housing section 1012 resides one or more printed circuit boards (PCB) (not shown), semiconductor chips (not shown), and/or other electronics (not shown) for performing operations related to the general purpose transformer monitoring device 1000. In one embodiment, the housing section 1012 is a substantially rectangular housing; however, differently sized and differently shaped housings may be used in other embodiments.

Additionally, the main unit 1001 further comprises one or more cables 1004, 1007. The cables 1004, 1007 may be coupled to a conductor cable or corresponding bus bars (not shown) and ground or reference voltage conductor (not shown), respectively, for the corresponding conductor cable, which will be described further herein.

Note that methods in accordance with an embodiment of the present disclosure use the described monitoring device 1000 for collecting current and/or voltage data. Further note that the monitoring device 1000 described is portable and easily connected and/or coupled to an electrical conductor and/or transformer posts. Due to the noninvasive method of installing the satellite unit and main unit around a conductor and connecting the leads 1004, 1007 to connection points, an operator (or utility personnel) need not de-energize a transformer 104, 121 for connection or coupling thereto. Further, no piercing (or other invasive technique) of the electrical line is needed during deployment to the power grid. Thus, the monitoring device 1000 is easy to install. Thus, deployment to the power grid is easy to effectuate.

During operation, the satellite unit 1021 and/or the main unit 1001 collects data indicative of current through a conductor cable. The satellite unit 1021 transmits its collected data via the cable 1011 to the main unit 1001. Additionally, the cables 1004, 1007 may be used to collect data indicative of voltage corresponding to a conductor cable about which the satellite unit is installed. The data indicative of the current and voltage sensed corresponding to the conductor may be used to calculate power usage.

As indicated hereinabove, there are a number of different methods that may be employed using the general purpose monitoring device 1000 in order to collect current and/or voltage data and calculate power usage.

In one embodiment, the general purpose transformer monitoring device 1000 may be used to collect voltage and current data from a three phase system (if multiple general purpose transformer monitoring devices 100 are used) or a single phase system.

With respect to a single phase system, the single phase system has two conductor cables and a neutral cable. For example, electricity supplied to a typical home in the United States has two conductor cables (or hot cables) and a neutral cable. Note that the voltage across the conductor cables in such an example is 240 Volts (the total voltage supplied) and the voltage across one of the conductor cables and the neutral is 120 Volts. Such an example is typically viewed as a single phase system.

In a three phase system, there are typically three conductor cables and a neutral cable (sometimes there may not be a neutral cable). In one system, voltage measured in each conductor cable is 120° out of phase from the voltage in the other two conductor cables. Multiple general purpose transformer monitoring devices 1000 can obtain current readings from each conductor cable and voltage readings between each of the conductor cables and the neutral (or obtain voltage readings between each of the conductor cables). Such readings may then be used to calculate power usage.

Note that the main unit 1001 of the general purpose transformer monitoring device 1000 further comprises one or more light emitting diodes (LEDs) 1003. The LEDs may be used by logic (not shown but referred to herein with reference to FIG. 4 as analytic logic 308) to indicate status, operations, or other functions performed by the general purpose transformer monitoring device 1000.

Figure 4:
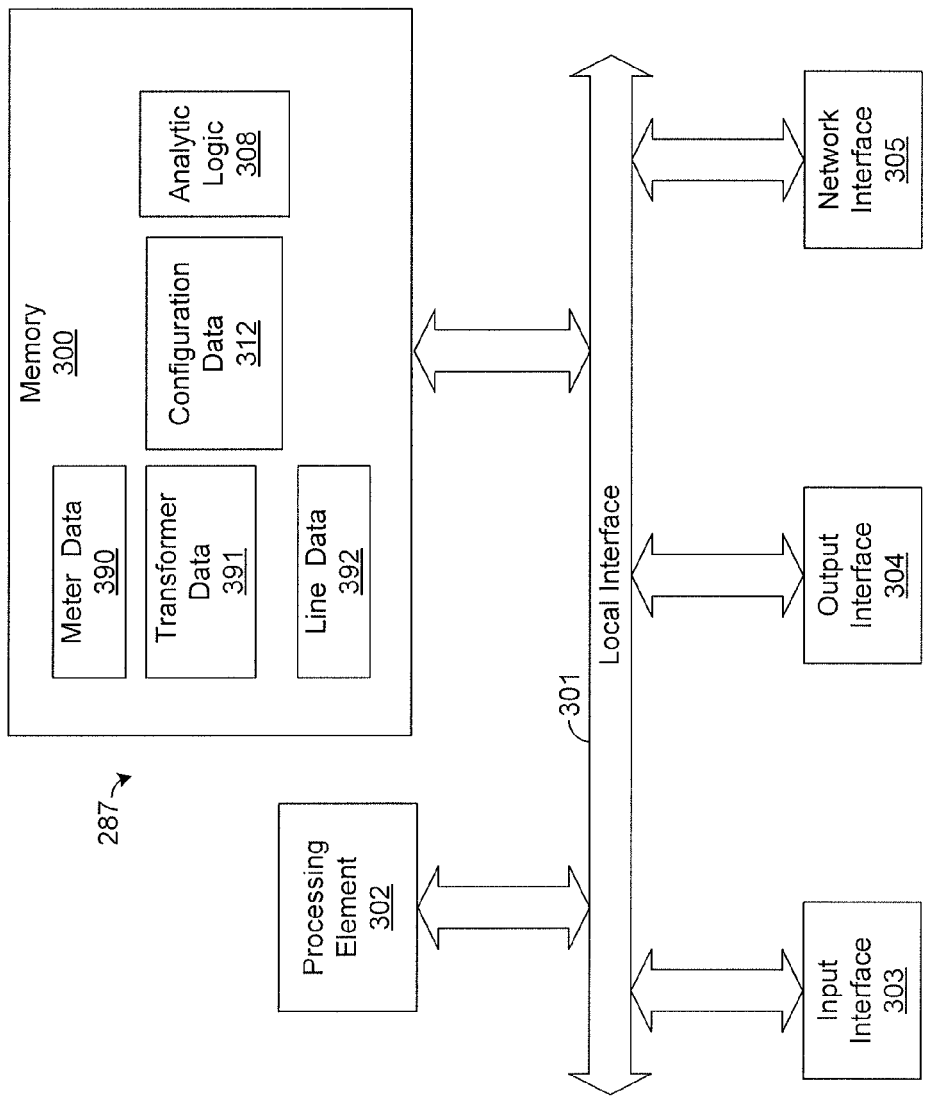
FIG. 4 is a block diagram depicting an exemplary operations computing device, such as is depicted in FIG. 2A.

FIG. 4 depicts an exemplary embodiment of the operations computing device 287 depicted in FIG. 2A. As shown by FIG. 4, the operations computing device 287 comprises analytic logic 308, meter data 390, transformer data 391, line data 392, and configuration data 312 all stored in memory 300.

The analytics logic 308 generally controls the functionality of the operations computing device 287, as will be described in more detail hereafter. It should be noted that the analytics logic 308 can be implemented in software, hardware, firmware or any combination thereof. In an exemplary embodiment illustrated in FIG. 4, the analytics logic 308 is implemented in software and stored in memory 300.

Note that the analytics logic 308, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

The exemplary embodiment of the operations computing device 287 depicted by FIG. 4 comprises at least one conventional processing element 302, such as a digital signal processor (DSP) or a central processing unit (CPU), that communicates to and drives the other elements within the operations computing device 287 via a local interface 301, which can include at least one bus. Further, the processing element 302 is configured to execute instructions of software, such as the analytics logic 308.

An input interface 303, for example, a keyboard, keypad, or mouse, can be used to input data from a user of the operations computing device 287, and an output interface 304, for example, a printer or display screen (e.g., a liquid crystal display (LCD)), can be used to output data to the user. In addition, a network interface 305, such as a modem, enables the operations computing device 287 to communicate via the network 280 (FIG. 2A) to other devices in communication with the network 280.

As indicated hereinabove, the meter data 390, the transformer data 391, the line data 392, and the configuration data 312 are stored in memory 300. The meter data 390 is data indicative of power usage measurements and/or other electrical characteristics obtained from each of the meters 112-117 (FIG. 1). In this regard, the meter data 390 is an aggregate representation of the meter data 935-940 (FIG. 2A) received from the meter data collection devices 986-991 (FIG. 2A).

In one embodiment, the analytics logic 308 receives the meter data 935-940 and stores the meter data 935-940 (as meter data 390) such that the meter data 935-940 may be retrieved based upon the transformer 104 or 121 (FIG. 1) to which the meter data's corresponding meter 112-117 is coupled. Note that meter data 390 is dynamic and is collected periodically by the meter data collection devices 986-991 from the meters 112-117. For example, the meter data 390 may include, but is not limited to, data indicative of current measurements, voltage measurements, and/or power calculations over a period of time per meter 112-117 and/or per transformer 104 or 121. The analytic logic 308 may use the collected meter data 390 to determine whether the amount of electricity supplied by the corresponding transformer 104 or 121 is substantially equal to the electricity that is received at the consumer premises 106-111.

In one embodiment, each entry of the meter data 935-940 in the meter data 390 is associated with an identifier (not shown) identifying the meter 112-117 (FIG. 1) from which the meter data 935-940 is collected. Such identifier may be randomly generated at the meter 112-117 via logic (not shown) executed on the meter 112-117.

In such a scenario, data indicative of the identifier generated by the logic at the meter 112-117 may be communicated, or otherwise transmitted, to the transformer monitoring device 243 or 244 to which the meter is coupled. Thus, when the transformer monitoring devices 243, 244 transmit transformer data 240, 241, each transformer monitoring device 243, 244 can also transmit its unique meter identifier (and/or the unique identifier of the meter that sent the transformer monitoring device 243, 244 the meter data). Upon receipt, the analytics logic 308 may store the received transformer data 240, 241 (as transformer data 391) and the unique identifier of the transformer monitoring device 243, 244 and/or the meter unique identifier such that the transformer data 391 may be searched on the unique identifiers when performing calculations. In addition, the analytics logic 308 may store the unique identifiers of the transformer monitoring devices 243, 244 corresponding to the unique identifiers of the meters 112-117 from which the corresponding transformer monitoring devices 243, 244 receive meter data. Thus, the analytics logic 308 can use the configuration data 312 when performing operations, such as aggregating particular meter data entries in meter data 390 to compare to transformer data 391.

The transformer data 391 is data indicative of aggregated power usage measurements obtained from the distribution transformers 104, 121. Such data is dynamic and is collected periodically. Note that the transformer data 240, 241 comprises data indicative of current measurements, voltage measurements, and/or power calculations over a period of time that indicates the amount of aggregate power provided to the consumer premises 106-111. Notably, the transformer data 391 comprises data indicative of the aggregate power that is being sent to a "group," i.e., two or more consumer premises being monitored by the transformer monitoring devices 243, 244, although the transformer data 391 can comprise power data that is being sent to only one consumer premises being monitored by the transformer monitoring device.

In one embodiment, during setup of a distribution network 119 (FIG. 1), the analytic logic 308 may receive data identifying the unique identifier for one or more transformers 104, 121. In addition, when a transformer monitoring device 243, 244 is installed and electrically coupled to one or more transformers 104, 121, data indicative of the unique identifier of the transformers 104, 121 may be provided to the meters 112-117 and/or to the operations computing device 287, as described hereinabove. The operations computing device 287 may store the unique identifiers (i.e., the unique identifier for the transformers) in configuration data 312 such that each meter 112-117 is correlated in memory with a unique identifier identifying the distribution transformer from which the consumer premises 106-111 associated with the meter 112-117 receives power.

The line data 273-275 is data indicative of power usage measurements obtained from the line data collection system 290 along transmission lines 101b-101d in the system 100. Such data is dynamic and is collected periodically. Note that the line data 273-274 comprises data indicative of current measurements, voltage measurements, and/or power calculations over a period of time that indicates the amount of aggregate power provided to the distribution substation transformer 103 and the distribution transformers 104, 121. Notably, the line data 392 comprises data indicative of the aggregate power that is being sent to a "group," i.e., one or more distribution substation transformers 103.

During operation, the analytic logic 308 receives meter data 935-940 via the network interface 305 from the network 280 (FIG. 2) and stores the meter data 935-940 as meter data 390 in memory 300. The meter data 390 is stored such that it may be retrieved corresponding to the distribution transformer 104, 121 supplying the consumer premise 106-111 to which the meter data corresponds. Note there are various methods that may be employed for storing such data including using unique identifiers, as described hereinabove, or configuration data 312, also described hereinabove.

The analytic logic 308 may perform a variety of functions to further analyze the power transmission and distribution system 100 (FIG. 1). As an example, and as discussed hereinabove, the analytic logic 308 may use the collected transformer data 391, line data 392, and/or meter data 390 to determine whether electricity theft is occurring along the transmission lines 101a, 101b or the distribution lines 101c-101j. In this regard, the analytic logic 308 may compare the aggregate power consumed by the group of consumer premises (e.g., consumer premises 106-108 or 109-111) and compare the calculated aggregate with the actual power supplied by the corresponding distribution transformer 104 or 121. In addition, the analytic logic 308 may compare the power transmitted to the distribution substation transformer 103 and the aggregate power received by the distribution transformers 104, 121, or the analytic logic 308 may compare the power transmitted to the transmission substation 102 and the aggregate power received by one or more distribution substation transformers 103.

If comparisons indicate that electricity theft is occurring anywhere in the power and distribution system 100, the analytics logic 308 may notify a user of the operations computing device 287 that there may be a problem. In addition, the analytics logic 308 can pinpoint a location in the power transmission and distribution system 100 where theft may be occurring. In this regard, the analytic logic 308 may have a visual or audible alert to the user, which can include a map of the system 100 and a visual identifier locating the problem.

As indicated hereinabove, the analytics logic 308 may perform a variety of operations and analysis based upon the data received. As an example, the analytic logic 308 may perform a system capacity contribution analysis. In this regard, the analytic logic 308 may determine when one or more of the consumer premises 106-111 have coincident peak power usage (and/or requirements). The analytics logic 308 determines, based upon this data, priorities associated with the plurality of consumer premises 106-111, e.g. what consumer premises requires a particular peak load and at what time. Loads required by the consumer premises 106-111 may necessarily affect system capacity charges; thus, the priority may be used to determine which consumer premises 106-111 may benefit from demand management.

Additionally, the analytic logic 308 may use the meter data 390 (FIG. 4), the transformer data 391, the line data 392, and the configuration data 312 (collectively referred to as "operations computing device data") to determine asset loading. For example, analyses may be performed for substation and feeder loading, transformer loading, feeder section loading, line section loading, and cable loading. Also, the operations computing device data may be used to produce detailed voltage calculations and analysis of the system 100 and/or technical loss calculations for the components of the system 100, and to compare voltages experienced at each distribution transformer with the distribution transformer manufacturer minimum/maximum voltage ratings and identify such distribution transformer(s) which are operating outside of the manufacturer's suggested voltages range thereby helping to isolate power sag and power swell instances, and identify distribution transformer sizing and longevity information.

In one embodiment, a utility company may install load control devices (not shown). In such an embodiment, the analytics logic 308 may use the operations computing device data to identify one or more locations of load control devices.

Figure 5:
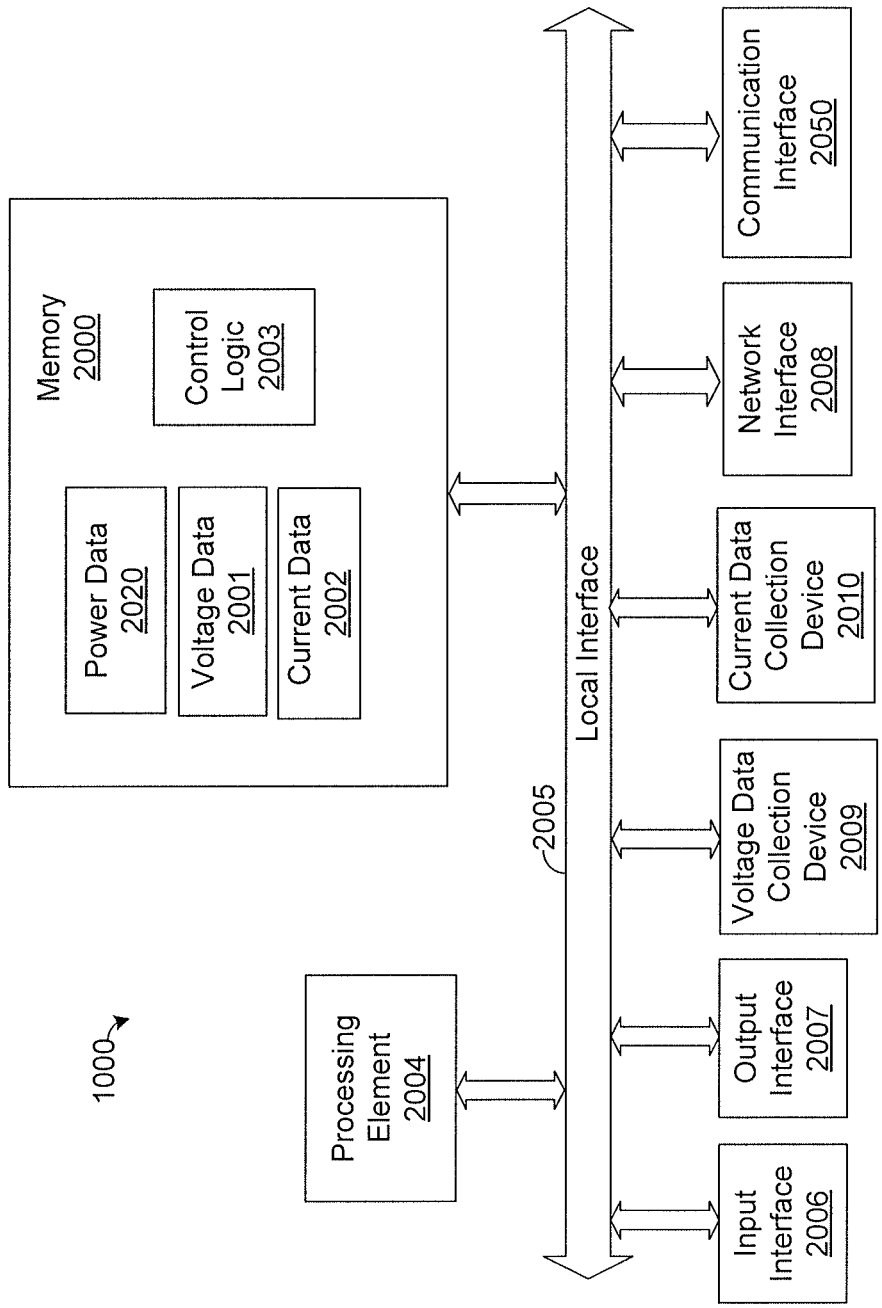
FIG. 5 is a block diagram depicting an exemplary transformer monitoring device, such as is depicted in FIG. 2A.

FIG. 5 depicts an exemplary embodiment of the transformer monitoring device 1000 depicted in FIG. 3. As shown by FIG. 5, the transformer monitoring device 1000 comprises control logic 2003, voltage data 2001, current data 2002, and power data 2020 stored in memory 2000.

The control logic 2003 controls the functionality of the operations transformer monitoring device 1000, as will be described in more detail hereafter. It should be noted that the control logic 2003 can be implemented in software, hardware, firmware or any combination thereof. In an exemplary embodiment illustrated in FIG. 5, the control logic 2003 is implemented in software and stored in memory 2000.

Note that the control logic 2003, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

The exemplary embodiment of the transformer monitoring device 1000 depicted by FIG. 5 comprises at least one conventional processing element 2004, such as a digital signal processor (DSP) or a central processing unit (CPU), that communicates to and drives the other elements within the transformer monitoring device 1000 via a local interface 2005, which can include at least one bus. Further, the processing element 2004 is configured to execute instructions of software, such as the control logic 2003.

An input interface 2006, for example, a keyboard, keypad, or mouse, can be used to input data from a user of the transformer monitoring device 1000, and an output interface 2007, for example, a printer or display screen (e.g., a liquid crystal display (LCD)), can be used to output data to the user. In addition, a network interface 2008, such as a modem or wireless transceiver, enables the transformer monitoring device 1000 to communicate with the network 280 (FIG. 2A).

In one embodiment, the transformer monitoring device 1000 further comprises a communication interface 2050. The communication interface 2050 is any type of interface that when accessed enables power data 2020, voltage data 2001, current data 2002, or any other data collected or calculated by the transformer monitoring device 100 to be communicated to another system or device. As an example, the communication interface may be a serial bus interface that enables a device that communicates serially to retrieve the identified data from the transformer monitoring device 1000. As another example, the communication interface 2050 may be a universal serial bus (USB) that enables a device configured for USB communication to retrieve the identified data from the transformer monitoring device 1000. Other communication interfaces 2050 may use other methods and/or devices for communication including radio frequency (RF) communication, cellular communication, power line communication, and WiFi communications. The transformer monitoring device 1000 further comprises one or more voltage data collection devices 2009 and one or more current data collection devices 2010. In this regard, with respect to the transformer monitoring device 1000 depicted in FIG. 3, the transformer monitoring device 1000 comprises the voltage data collection device 2009 that may include the cables 1004, 1007 (FIG. 3) that sense voltages at nodes (not shown) on a transformer to which the cables are attached. As will be described further herein, the control logic 2003 receives data via the cables 1004, 1007 indicative of the voltages at the nodes and stores the data as voltage data 2001. The control logic 2003 performs operations on and with the voltage data 2001, including periodically transmitting the voltage data 2001 to, for example, the operations computing device 287 (FIG. 2A).

Further, with respect to the transformer monitoring device 1000 depicted in FIG. 3, the transformer monitoring device 1000 comprises the current sensors (not shown) contained in the sensing unit housing 1005 (FIG. 3) and the sensing unit housing section 1018 (FIG. 3), which are described hereinabove. The current sensors sense current traveling through conductor cables (or neutral cables) around which the sensing unit housings 1005, 1018 are coupled. As will be described further herein, the control logic 2003 receives data indicative of current from the satellite sensing unit 1021 (FIG. 3) via the cable 1011 and data indicative of the current from the current sensor of the main unit 1001 contained in the sensing unit housing section 1018. The control logic 2003 stores the data indicative of the currents sensed as the current data 2002. The control logic 2003 performs operations on and with the current data 2002, including periodically transmitting the voltage data 2001 to, for example, the operations computing device 287 (FIG. 2A).

Note that the control logic 2003 may perform calculations with the voltage data 2001 and the current data 2002 prior to transmitting the voltage data 2001 and the current data 2002 to the operations computing device 287. In this regard, for example, the control logic 2003 may calculate power usage using the voltage data 2001 and current data 2002 over time and periodically store resulting values as power data 2020.

During operations, the control logic 2003 may transmit data to the operations computing device 287 via the cables via a power line communication (PLC) method. In other embodiments, the control logic 2003 may transmit the data via the network 280 (FIG. 2A) wirelessly or otherwise.

Figure 6:
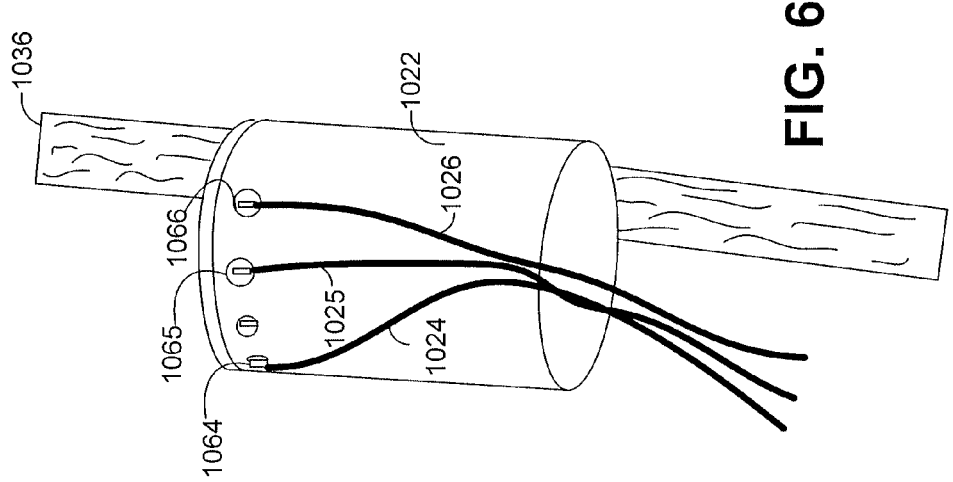
FIG. 6 is a drawing of a transformer can in accordance with an embodiment of the present disclosure.

FIGS. 6-10 depict one exemplary practical application, use, and operation of the transformer monitoring device 1000 shown in the drawing in FIG. 3. In this regard, FIG. 6 is a transformer can 1022, which houses a transformer (not shown), mounted on a utility pole 1036. One or more cables 1024-1026 carry current from the transformer can 1022 to a destination (not shown), e.g., consumer premises 106-111 (FIG. 1). The cables 1024-1026 are connected to the transformer can at nodes 1064-1066. Each node 1064-1066 comprises a conductive connector (part of which is sometimes referred to as a bus bar).

Figure 7:
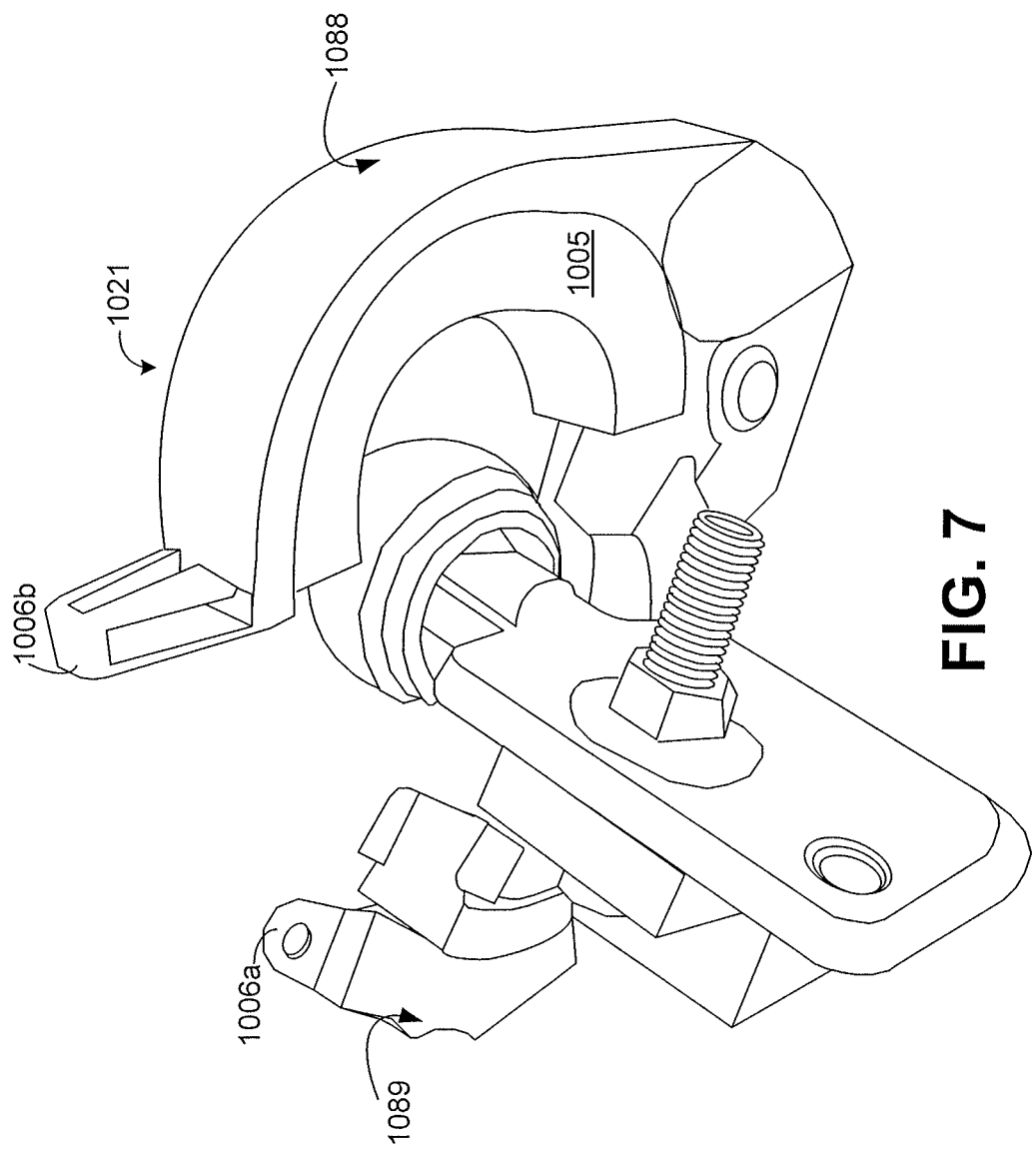
FIG. 7 is a drawing showing a satellite unit of the transformer monitoring device depicted in FIG. 3 being installed on the transformer can depicted in FIG. 6.
Figure 8:
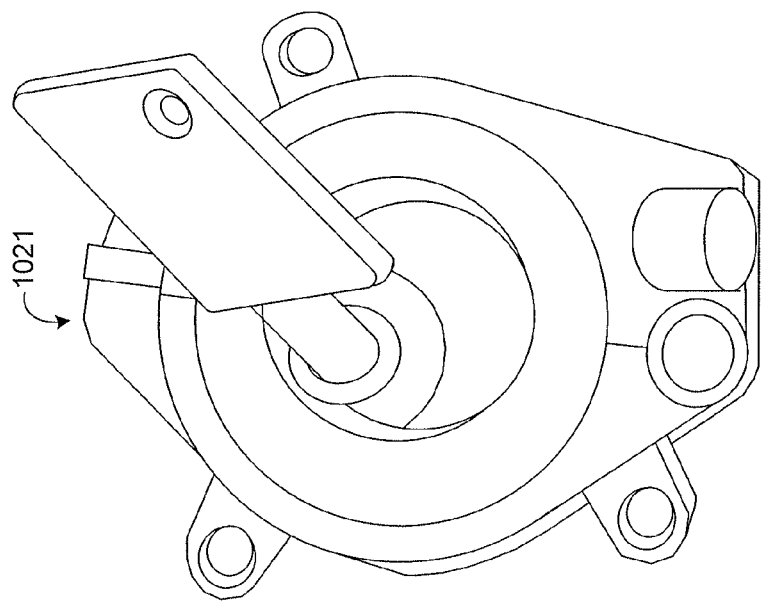
FIG. 8 is a drawing showing the satellite unit of the transformer monitoring device depicted in FIG. 3 installed on the transformer can depicted in FIG. 6.

FIG. 7 depicts the satellite unit 1021 of the transformer monitoring device 1000 being placed on one of the nodes 1064-1066 (FIG. 6), i.e., in an open position. A technician (not shown), e.g., an employee of a utility company (not shown), decouples the latch 1006 (FIG. 3), made up by decoupled sections 1006a and 1006b, and places the sections 1088 and 1089 around a portion of the node 1064-1066 such that the sensor unit (not shown) interfaces with the node and senses a current flowing through the node. FIG. 8 depicts the satellite unit 1021 of the transformer monitoring device 1000 latched around the node 1064-1066 in a closed position.

Figure 9:
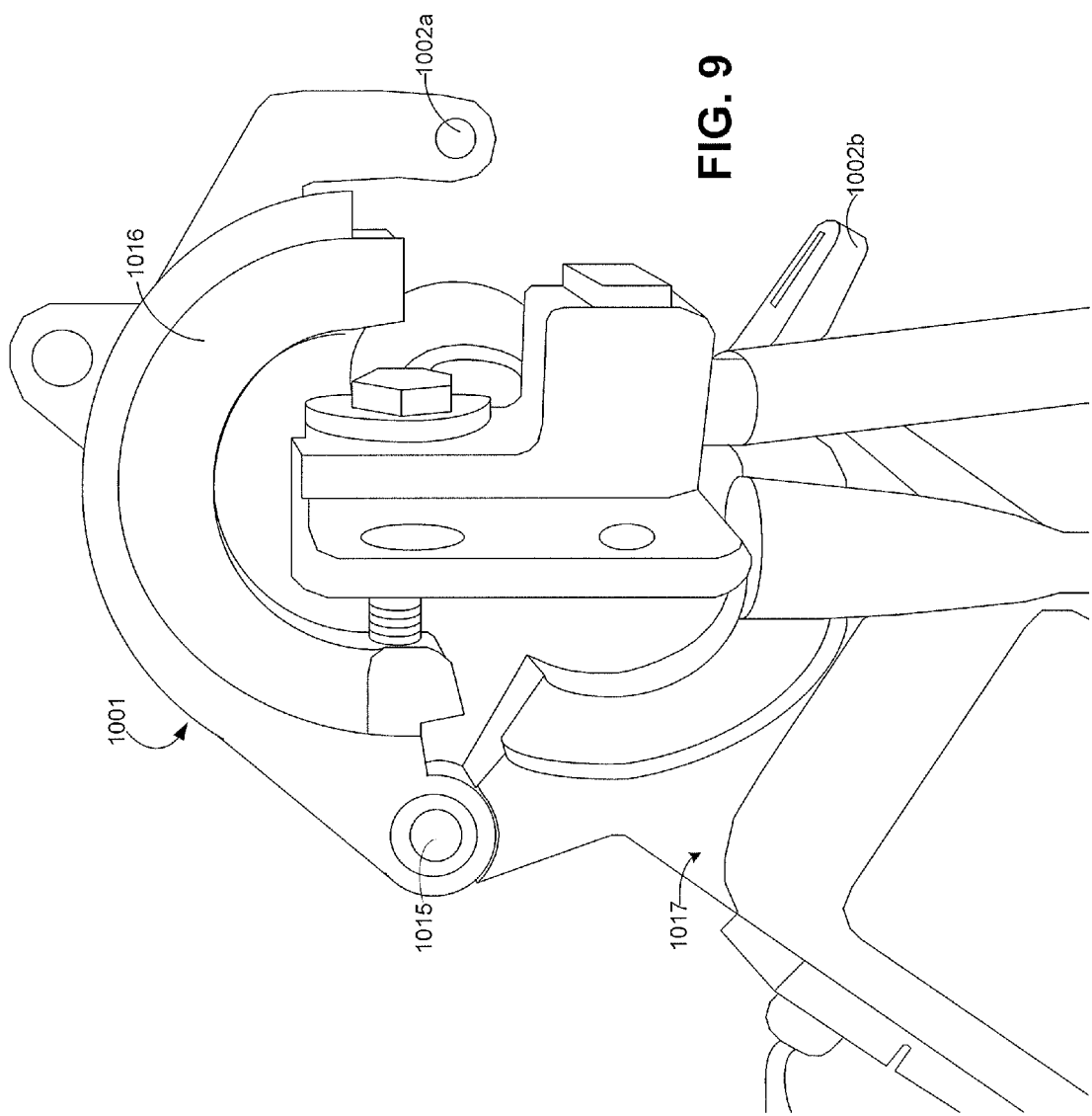
FIG. 9 is a drawing showing a main unit of the transformer monitoring device depicted in FIG. 3 installed on the transformer can depicted in FIG. 6.
Figure 10:
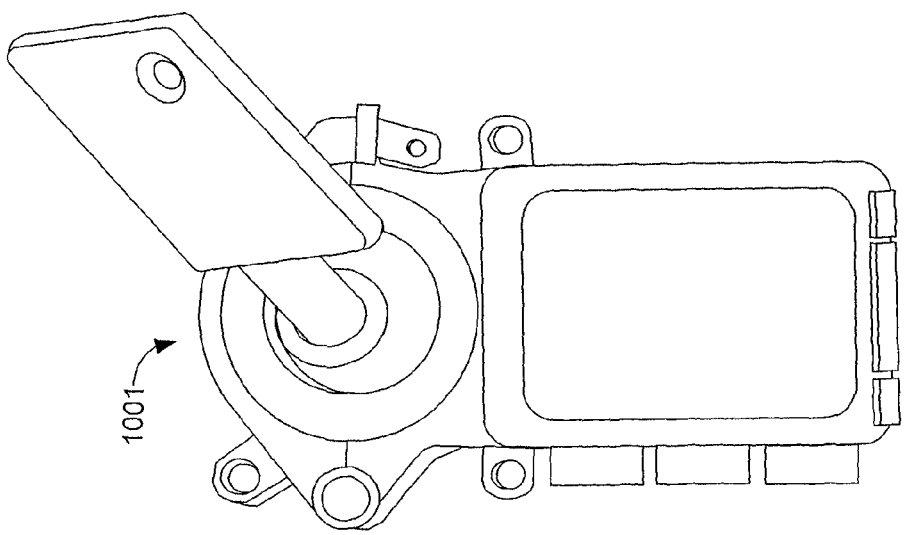
FIG. 10 is a drawing showing a main unit of the transformer monitoring device depicted in FIG. 8 installed on the transformer can depicted in FIG. 6.

FIG. 9 depicts the main unit 1001 of the transformer monitoring device 1000 being placed on one of the nodes 1064-1066, i.e., in an open position. The technician decouples the latch 1002, made up by decoupled sections 1002a and 1002b, and places the sections 1016 and 1017 around a portion of the node 1064-1066 such that the sensor unit (not shown) interfaces with the node and senses a current flowing through the node. FIG. 10 is a drawing of the transformer monitoring device 1000 latched around the node 1064-1066. FIG. 10 depicts the main unit 1001 of the transformer monitoring device 1000 latched around the node 1064-1066 and in a closed position.

In one embodiment, the cables 1004, 1007 (FIG. 3) of the main unit 1001 may be connected to one of the nodes 1064-1066 about which the respective satellite unit 1021 is coupled and one of the nodes 1064-1066 about which the main unit 1001 is coupled. In this regard, as described hereinabove, the cable 1004 comprises a plurality of separate and distinct cables. One cable is connected to the node about which the satellite unit 1021 is coupled, and one cable is connected to the node about which the main unit 1001 is coupled.

During operation, the current detection device contained in the sensing unit housings 1005, 1018 (FIG. 3) sense current from the respective nodes to which they are coupled. Further, the connections made by the cables 1004, 1007 to the nodes and reference conductor sense the voltage at the respective nodes, i.e., the node around which the main unit is coupled and the node around which the satellite unit is coupled.

In one embodiment, the analytic logic 308 receives current data for each node and voltage data from each node based upon the current sensors and the voltage connections. The analytics logic 308 uses the collected data to calculate power over a period of time, which the analytic logic 308 transmits to the operations computing device 287 (FIG. 2A). In another embodiment, the analytic logic 308 may transmit the voltage data and the current data directly to the operations computing device 287 without performing any calculations.

Figure 11:
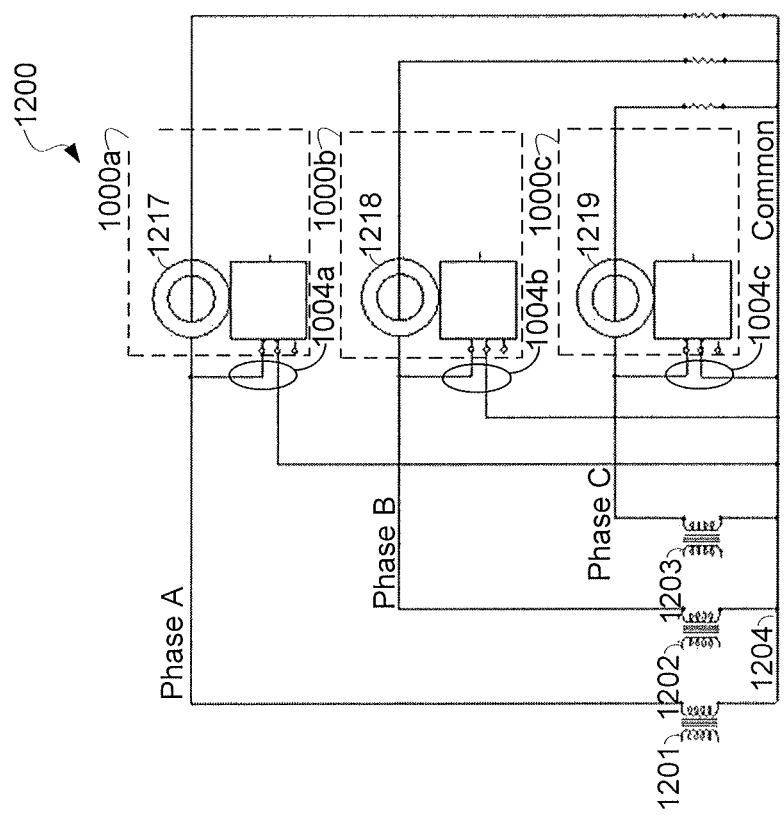
FIG. 11 is a diagram depicting a method of monitoring power in accordance with the system such as is depicted in FIG. 1 for a wye transformer configuration.
Figure 12:
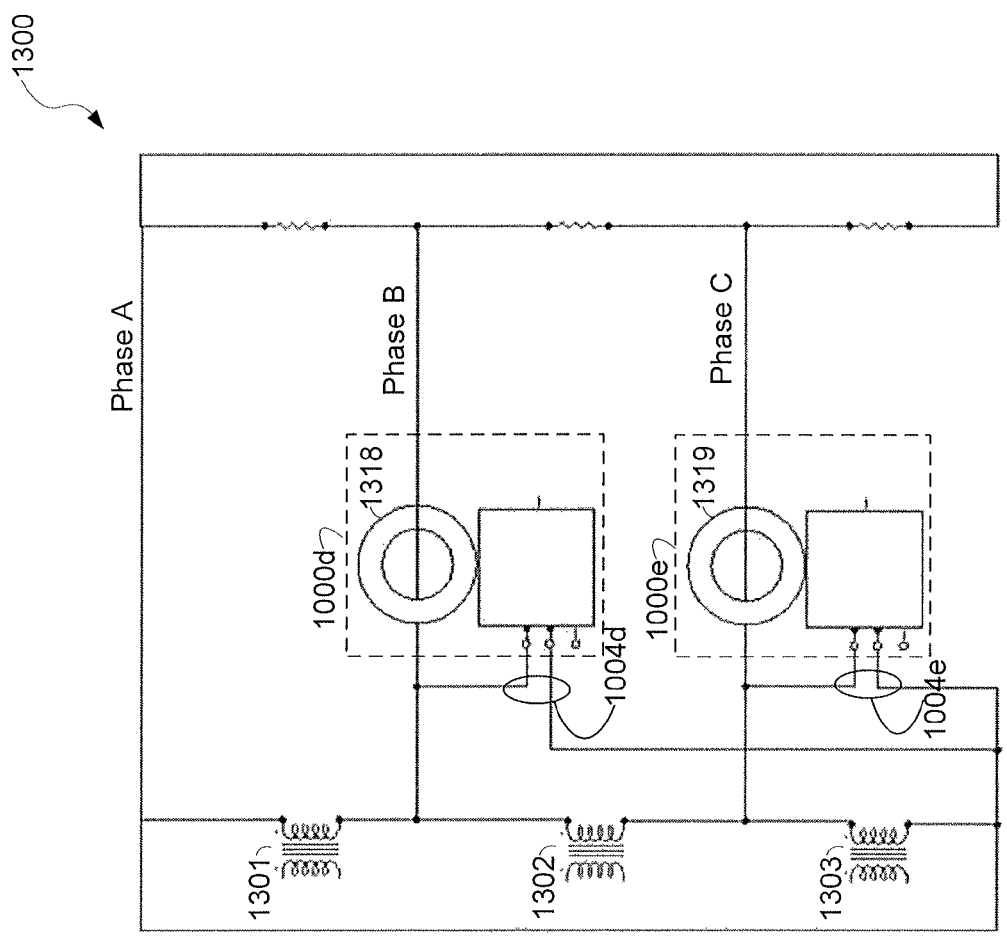
FIG. 12 is a diagram depicting a method of monitoring power in accordance with the system such as is depicted in FIG. 1 for a Delta transformer configuration.
Figure 13:
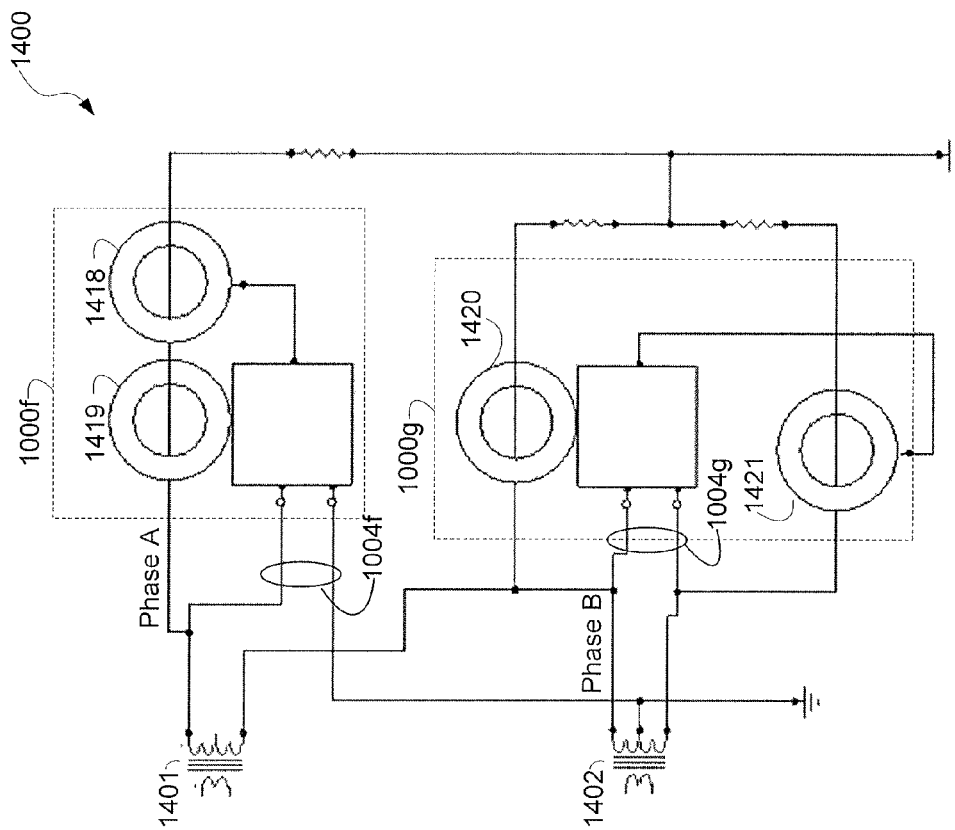
FIG. 13 is a diagram depicting a method of monitoring power in accordance with the system such as is depicted in FIG. 1 for an Open Delta transformer configuration.

FIGS. 11-13 further illustrate methods that may be employed using the monitoring device 1000 FIG. 3 in a system 100 (FIG. 1). As described hereinabove, the monitoring device 1000 may be coupled to a conductor cable (not shown) or a bushing (not shown) that attaches the conductor cable to a transformer can 1022 (FIG. 6). In operation, the transformer monitoring device 1000 obtains a current and voltage reading associated with the conductor cable to which it is coupled, as described hereinabove, and the main unit 1001 (FIG. 3) uses the current reading and the voltage reading to calculate power usage.

Note for purposes of the discussion hereinafter, a transformer monitoring device 1000 (FIG. 3) comprises two current sensing devices, including one contained in housing 1005 (FIG. 3) and one contained in the housing 1018 (FIG. 3) of the satellite unit 1021 (FIG. 3) and the main unit 1001 (FIG. 3), respectively.

FIG. 11 is a diagram depicting a distribution transformer 1200 for distributing three-phase power, which is indicative of a "wye" configuration. In this regard, three-phase power comprises three conductors providing AC power such that the AC voltage waveform on each conductor is 120° apart relative to each other, where 360° is approximately one sixtieth of a second. As described hereinabove, three-phase power is transmitted on three conductor cables and is delivered to distribution substation transformer 103 (FIG. 1) and distribution transformer 104 (FIG. 1) on three conductor cables. Thus, the receiving distribution transformer 104 has three winding pairs (one for each phase input voltage received) to transform the voltage of the power received to a level of voltage needed for delivery to the consumers 106-108 (FIG. 1).

In the distribution transformer 1200, three single-phase transformers 1201-1203 are connected to a common (neutral) lead 1204. For purposes of illustration, each transformer connection is identified as a phase, e.g., Phase A/transformer 1201, Phase B/transformer 1202, and Phase C/transformer 1203.

In the embodiment depicted in FIG. 11, three monitoring devices 1000a, 1000b, and 1000c (each configured substantially similar to monitoring device 1000 (FIG. 3)) are employed to obtain data (e.g., voltage and current data) used to calculate the power at the distribution transformer 1200.

In this regard, at least one of current sensing devices 1217 of monitoring device 1000a is used to collect current data for Phase A. Notably, the sensing device 1217 of the monitoring device 1000a used to collect current data may be housed in the satellite unit 1021 (FIG. 3) or the main unit 1001 (FIG. 3). The voltage lead 1004a of the monitoring device 1000a is connected across the Phase A conductor cable and common 1204 in order to obtain voltage data. Note that in one embodiment both current sensing devices in the satellite unit 1021 and the main unit 1001 (current sensing device 1217) may be coupled around the Phase A conductor cable.

Further, a current sensing device 1218 of monitoring device 1000b is used to collect current data for Phase B. As described above with reference to Phase A, the sensing device 1218 of the monitoring device 1000b used to collect current data may be housed in the satellite unit 1021 (FIG. 3) or the main unit 1001 (FIG. 3). The voltage lead 1004b of the monitoring device 1000b is connected across the Phase B conductor cable and common 1204 in order to obtain voltage data. Similar to the Phase A implementation described above, in one embodiment both current sensing device in the satellite unit 1021 and the main unit 1001 (current sensing device 1218) may be coupled around the Phase B conductor cable.

Additionally, a current sensing device 1219 of monitoring device 1000c is used to collect voltage and current data for Phase C. As described above with reference to Phase A, the sensing device 1219 of the monitoring device 1000c that is used to collect current data may be housed in the satellite unit 1021 (FIG. 3) or the main unit 1001 (FIG. 3). The voltage lead 1004c of the monitoring device 1000c is connected across the Phase C conductor cable and common 1204 in order to obtain voltage data. Similar to the Phase A implementation described above, in one embodiment both current sensing devices in the satellite unit 1021 and the main unit 1001 (current sensing device 1219) may be coupled around the Phase C conductor cable.

During monitoring, control logic 2003 (FIG. 5) of the monitoring devices 1000a-1000c use current measurements and voltage measurements to calculate total power. As described hereinabove, the power calculated from the measurements made by the transformer monitoring devices 1000a, 1000b, and 1000c may be used in various applications to provide information related to the power transmission and distribution system 100 (FIG. 1).

FIG. 12 is a diagram depicting a distribution transformer 1300 for distributing three-phase power, which is indicative of a delta configuration. Such distribution transformer 1300 may be used as the distribution transformer 104 (FIG. 1). The distribution transformer 1300 (similar to the distribution transformer 1200 (FIG. 11)) has three single phase transformers to transform the voltage of the power received on three conductor cables (i.e., three-phase power) to a level of voltage needed for delivery to the consumers 106-108 (FIG. 1).

The distribution transformer 1300 comprises three single-phase transformers 1301-1303. For purposes of illustration, each transformer connection is identified as a phase, e.g., Phase A/transformer 1301-transformer 1303, Phase B/transformer 1302-transformer 1301, and Phase C/transformer 1303-transformer 1302.

In the embodiment depicted in FIG. 12, two transformer monitoring devices 1000d and 1000e are employed to obtain voltage and current data, which are used to calculate power at the distribution transformer 1300. In this regard, transformer monitoring device 1000d is coupled about one of three incoming conductor cables, identified in FIG. 12 as Phase B, and transformer monitoring device 1000e is coupled about another one of the three incoming conductor cables, identified in FIG. 12 as Phase C. The monitoring devices 1000d and 1000e (each configured substantially similar to monitoring device 1000 (FIG. 3)) are employed to obtain data (e.g., voltage and current data) used to calculate the power at the distribution transformer 1300.

In this regard, a current sensing device 1318 of monitoring device 1000d is used to collect current data for Phase B. Notably, the sensing device 1318 of the monitoring device 1000d used to collect current data may be housed in the satellite unit 1021 (FIG. 3) or the main unit 1001 (FIG. 3). The voltage leads 1004d of the monitoring device 1000d are connected across the Phase B conductor cable and the Phase A conductor cable which measures a voltage differential. Note that in one embodiment both current sensing devices in the satellite unit 1021 and the main unit 1001 (current sensing device 1318) may be coupled around the Phase B conductor cable. Further note that in the delta configuration, Phase A may be arbitrarily designated as a "common" such that power may be calculated based on the voltage differentials between the current-sensed conductor cables and the designated "common," which in the present embodiment is Phase A.

Further, similar to Phase B measurements, a current sensing device 1319 of monitoring device 1000e is used to collect current data for Phase C. As described above with reference to Phase B, the sensing device 1319 of the monitoring device 1000e used to collect current data may be housed in the satellite unit 1021 (FIG. 3) or the main unit 1001 (FIG. 3). The voltage leads 1004e of the monitoring device 1000e are connected across the Phase C conductor cable and Phase A conductor cable. Notably, in one embodiment both current sensing devices in the satellite unit 1021 and the main unit 1001 (current sensing device 1319) may be coupled around the Phase C conductor cable.

During monitoring, control logic 2003 (FIG. 5) of the monitoring devices 1000d and 1000e use current measurements and voltage measurements to calculate total power. As described hereinabove, the power calculated from the measurements made by the transformer monitoring devices 1000f and 1000g may be used in various applications to provide information related to the power transmission and distribution system 100 (FIG. 1).

FIG. 13 is a diagram depicting a distribution transformer 1400 for distributing power, which is indicative of an open delta configuration. The distribution transformer 1400 has two single phase transformers to transform the voltage received to a level of voltage needed for delivery to the consumers 106-108 (FIG. 1).

The distribution transformer 1400 comprises two single-phase transformers 1401-1402. In the embodiment depicted in FIG. 13, two transformer monitoring devices 1000f and 1000g are employed to obtain voltage and current data, which are used to calculate power at the distribution transformer 1400.

Transformer monitoring device 1000f is coupled about one of three conductor cables identified in FIG. 13 as Phase A and transformer monitoring device 1000g is coupled about another one of the conductor cables identified in FIG. 13 as Phase B. The monitoring devices 1000f and 1000g (each configured substantially similar to monitoring device 1000 (FIG. 3)) are employed to obtain data (e.g., voltage and current data) used to calculate the power at the distribution transformer 1400.

In this regard, at least one of the current sensing devices 1418 or 1419 of monitoring device 1000f is used to collect voltage and current data for Phase A. While both sensing devices are shown coupled about Phase A, both are not necessarily needed in other embodiments. Notably, a sensing device of the monitoring device 1000f used to collect current data may be housed in the satellite unit 1021 (FIG. 3) or the main unit 1001 (FIG. 3). The voltage leads 1004f of the monitoring device 1000f are connected across the Phase A conductor cable and ground. Note that in one embodiment both current sensing devices in the satellite unit 1021 and the main unit 1001 may be coupled around the Phase A conductor cable, as shown.

Further, current sensing device 1420 housed in the main unit 1001 (FIG. 3) of monitoring device 1000g and current sensing device 1421 housed in the satellite unit 1021 (FIG. 3) of monitoring device 1000g is used to collect current data for Phase B. The voltage lead 1004g of the monitoring device 1000g is connected across the voltage outputs of the secondary of transformer 1402.

During monitoring, control logic 2003 (FIG. 5) of the transformer monitoring devices 1000f and 1000g uses current measurements and voltage measurements to calculate total power. As described hereinabove, the power calculated from the measurements made by the transformer monitoring devices 1000f and 1000g may be used in various applications to provide information related to the power transmission and distribution system 100 (FIG. 1).

Figure 14:
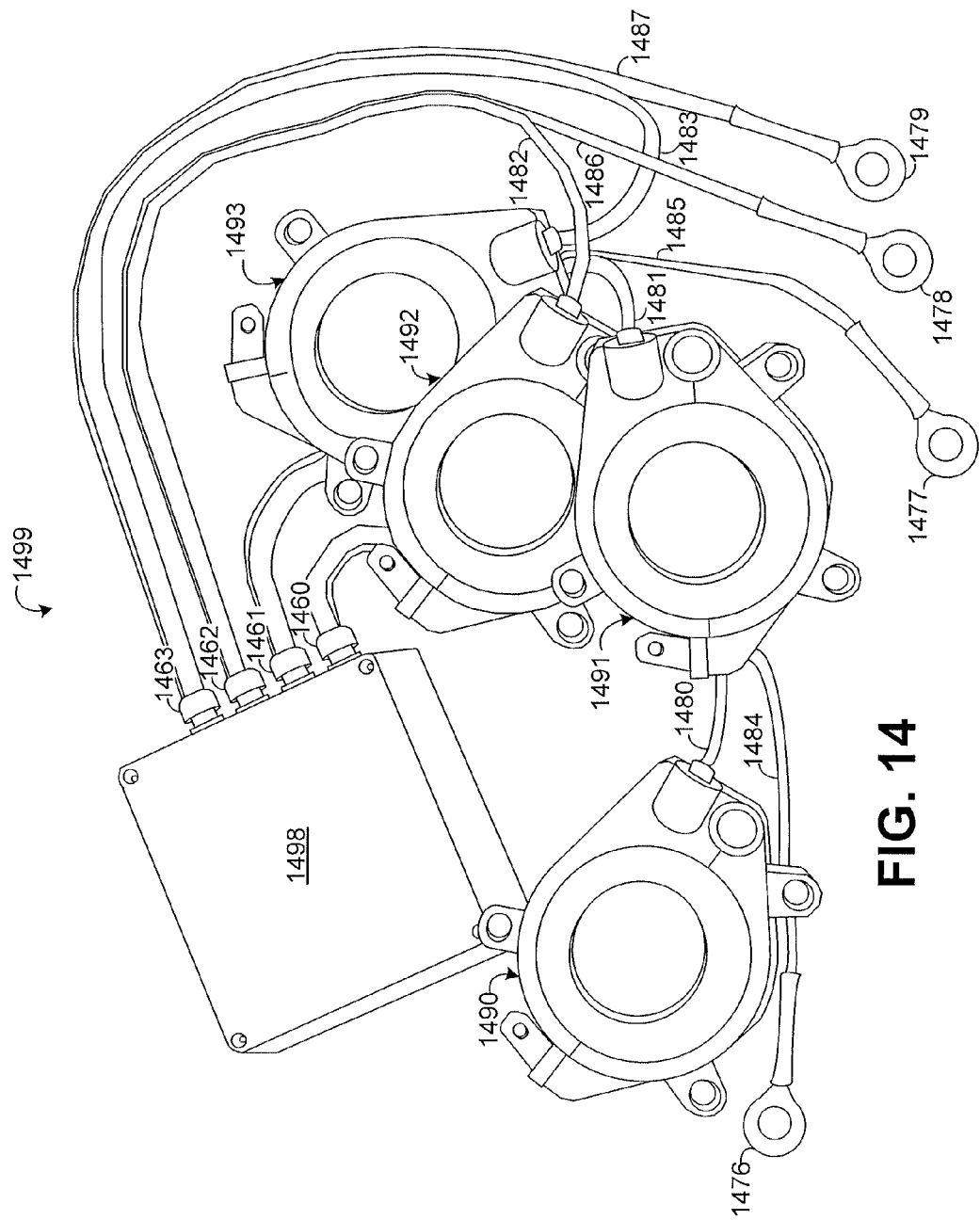
FIG. 14 is depicts a polyphase distribution transformer monitoring (PDTM) device in accordance with an embodiment of the present disclosure.

FIG. 14 depicts an exemplary polyphase distribution transformer monitor (PDTM) 1499 in accordance with an embodiment of the present disclosure. For purposes of this disclosure, in one embodiment, polyphase refers to a system for distributing alternating current electrical power and has three or more electrical conductors wherein each carries alternating currents having time offsets one from the others. Note that while the PDTM 1499 is configured to monitor up to four conductors (not shown), the PDTM may be used to monitor one or more conductors, e.g., single phase or two-phase power, which is substantially similar to monitoring three-phase power, which is described further herein.

Notably, with reference to FIG. 2A, the PDTM 1499 may serve the purpose and functionality and is a type of transformer monitoring device 244, 243 (FIG. 2A). Thus, the PDTM collects power and electrical characteristic data related to a particular distribution transformer 104, 121 (FIG. 1).

The PDTM 1499 comprises a control box 1498, which is a housing that conceals a plurality of electronic components, discussed further herein, that control the PDTM 1499. Additionally, the PDTM comprises a plurality of satellite current sensors 1490-1493.

The satellite current sensors 1490-1493 are structurally and functionally substantially similar to the satellite unit 1021 described with reference to FIGS. 3, 7, and 8. In this regard, the satellite current sensors 1490-1493 detect a current through an electrical cable, bus bar, or any other type of node through which current passes into and/or from a distribution transformer, such as the distribution transformer shown in FIG. 6.

Further, the satellite current sensors 1490-1493 are electrically connected to the control box 1498 (and to the electronics (not shown) contained therein). In this regard, the satellite current sensor 1490 may be electrically connected via connectors 1464, 1460 on the satellite current sensor 1490 and the control box 1498, respectively, by a voltage current cable 1480. Similarly, the satellite current sensor 1491 is electrically connected via connectors 1465, 1461 on the satellite current sensor 1491 and the control box 1498, respectively, by a voltage current cable 1481, the satellite current sensor 1492 is electrically connected via connectors 1466, 1462 on the satellite current sensor 1492 and the control box 1498, respectively, by a voltage current cable 1482, and the satellite current sensor 1493 is electrically connected via connectors 1467, 1463 on the satellite current sensor 1493 and the control box 1498, respectively, by a voltage current cable 1483.

Note that the current cables 1480-1483 may be an American National Standards Institute (ANSI)-type cable. In this regard, the current cables 1480-1483 may be either insulated or non-insulated. The current cables 1480-1483 may be any other type of cable known in the art or future-developed from transferring data indicative of current measurements made by the satellite current sensors 1490-1493 to the control box 1498.

In addition, each current cable 1480-1483 is further associated and electrically correlated with a voltage cable 1484-1487. In this regard, each voltage cable 1484 extends from the connectors 1460-1463 on the control box 1498 and terminates with ring terminals 1476-1479, respectively.

Note that in one embodiment of the PDTM 1499, connectors 1460-1463 may be unnecessary. In this regard, the conductors 1480-1483 and conductors 1484-1487 may be connected to electronics directly without use of the connectors 1460-1463.

During operation, one or more of the satellite current sensors 1490-1493 are installed about conductors (e.g., cables), bus bars, or other type of node through which current travels. In addition, each of the ring terminals 1476-1479, respectively, are coupled to the conductor, bus bar, or other type of node around which their respective satellite current sensor 1490-1493 is installed.

More specifically, each satellite current sensor 1490-1493 takes current measurements over time of current that is flowing through the conductor cable, bus bar, or node around which it is installed. Also, over time, voltage measurements are sensed via each of the satellite current sensors' respective voltage cables 1484-1487. As will be described herein, the current measurements and voltage measurements taken over time are correlated and thus used in order to determine power usage corresponding to the particular conductor cable, bus bar, or particular node.

Figure 15A:
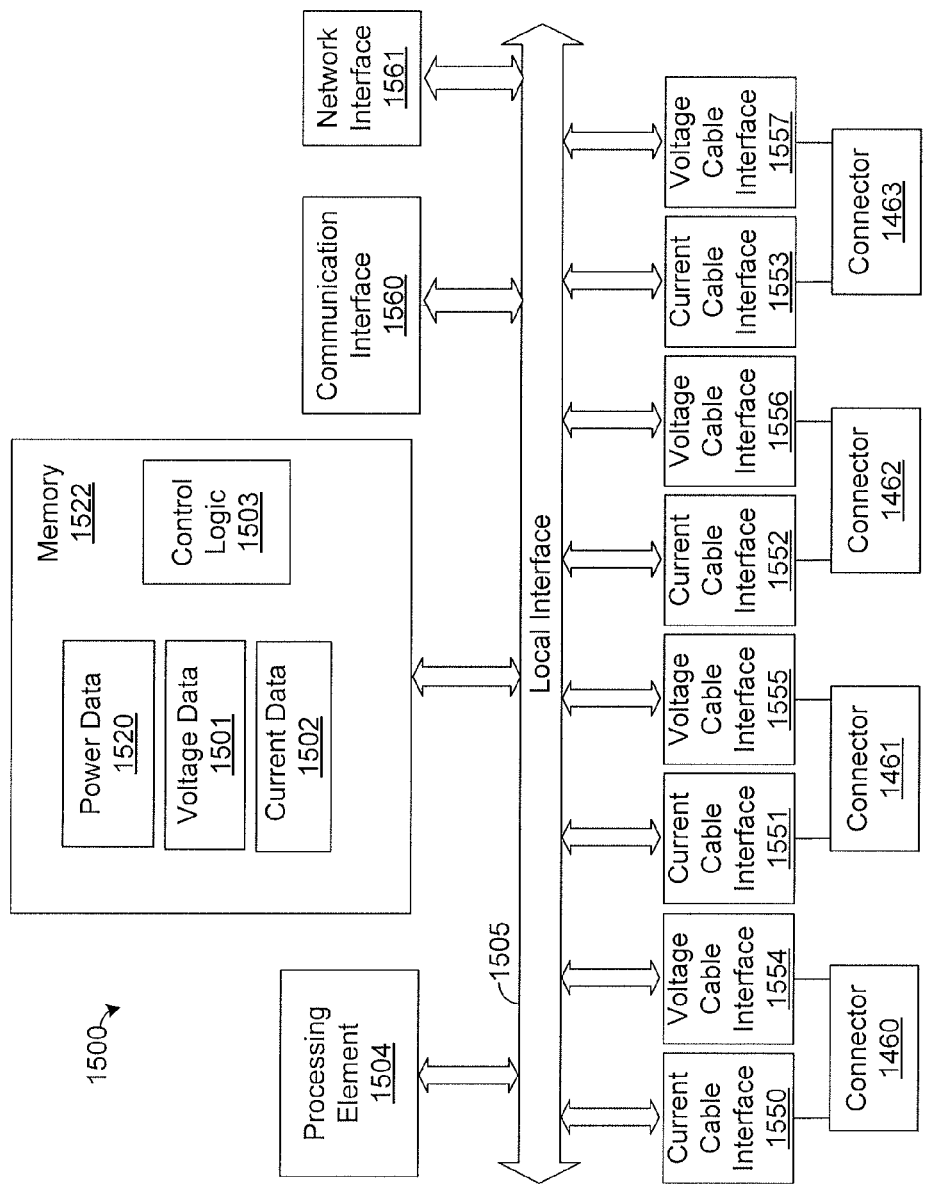
FIG. 15A is block diagram depicting an exemplary PDTM device, such as is depicted in FIG. 14.

FIG. 15A depicts an exemplary embodiment of a controller 1500 that is housed within the control box 1498. As shown by FIG. 15A, the controller 1500 comprises control logic 1503, voltage data 1501, current data 1502, and power data 1520 stored in memory 1522.

The control logic 1503 controls the functionality of the controller 1500, as will be described in more detail hereafter. It should be noted that the control logic 1503 can be implemented in software, hardware, firmware or any combination thereof. In an exemplary embodiment illustrated in FIG. 15, the control logic 1503 is implemented in software and stored in memory 1522.

Note that the control logic 1503, when implemented in software, can be stored and transported on any computer-readable medium for use by or in connection with an instruction execution apparatus that can fetch and execute instructions. In the context of this document, a "computer-readable medium" can be any means that can contain or store a computer program for use by or in connection with an instruction execution apparatus.

The exemplary embodiment of the controller 1500 depicted by FIG. 15 comprises at least one conventional processing element 1504, such as a digital signal processor (DSP) or a central processing unit (CPU), that communicates to and drives the other elements within the controller 1500 via a local interface 1505, which can include at least one bus. Further, the processing element 1504 is configured to execute instructions of software, such as the control logic 1503.

In addition, a network interface 1561, such as a modem or wireless transceiver, enables the controller 1500 to communicate with the network 280 (FIG. 2A).

In one embodiment, the controller 1500 further comprises a communication interface 1560. The communication interface 1560 is any type of interface that when accessed enables power data 1520, voltage data 1501, current data 1502, or any other data collected or calculated by the controller 1500 to be communicated to another system or device.

As an example, the communication interface 1560 may be a serial bus interface that enables a device that communicates serially to retrieve the identified data from the controller 1500. As another example, the communication interface 1560 may be a universal serial bus (USB) that enables a device configured for USB communication to retrieve the identified data from the controller 1500. Other communication interfaces may use other methods and/or devices for communication including radio frequency (RF) communication, cellular communication, power line communication, and Wi-Fi communications.

The controller 1500 further comprises one or more current cable interfaces 1550-1553 and voltage cable interfaces 1554-1557 that receive data transmitted via the current cables 1480-1483 and voltage cables 1484-1487, respectively. In this regard, each current cable interface/voltage cable interface pair is associated with a single connector. For example, connector 1460 receives cables 1480 (current) and 1484 (voltage), and the current cable interface 1550 receives data indicative of current and the voltage cable interface 1554 receives data indicative of current associated with the conductor about which the satellite current sensor 1490 is installed.

Similarly, connector 1461 receives cables 1481(current) and 1485(voltage), and the current cable interface 1551 receives data indicative of current and the voltage cable interface 1555 receives data indicative of current associated with the conductor about which the satellite current sensor 1491 is installed. The connector 1462 receives cables 1482 (current) and 1486(voltage), and the current cable interface 1552 receives data indicative of current and the voltage cable interface 1556 receives data indicative of current associated with the conductor about which the satellite current sensor 1492 is installed. Finally, connector 1463 receives cables 1483(current) and 1487(voltage), and the current cable interface 1553 receives data indicative of current and the voltage cable interface 1557 receives data indicative of current associated with the conductor about which the satellite current sensor 1493 is installed.

During operation, the control logic 1503 receives the voltage and current data from the interfaces 1550-1557 and stores the current data as current data 1502 and the voltage data as voltage data 1501. The control logic 1503 performs operations on and with the voltage data 1501 and current data 1502, including periodically transmitting the voltage data 1501 and current data 1502 to, for example, the operations computing device 287 (FIG. 2A).

Note that the control logic 1503 may perform calculations with the voltage data 1501 and the current data 1502 prior to transmitting the voltage data 1501 and the current data 1502 to the operations computing device 287. In this regard, for example, the control logic 2003 may calculate power usage using the voltage data 1501 and current data 1502 over time and periodically store resulting values as power data 1520.

During operations, the control logic 1503 may transmit data to the operations computing device 287 via the cables using a power line communication (PLC) method. In other embodiments, the control logic 1503 may transmit the data via the network 280 (FIG. 2A) wirelessly or otherwise.

Figure 15B:
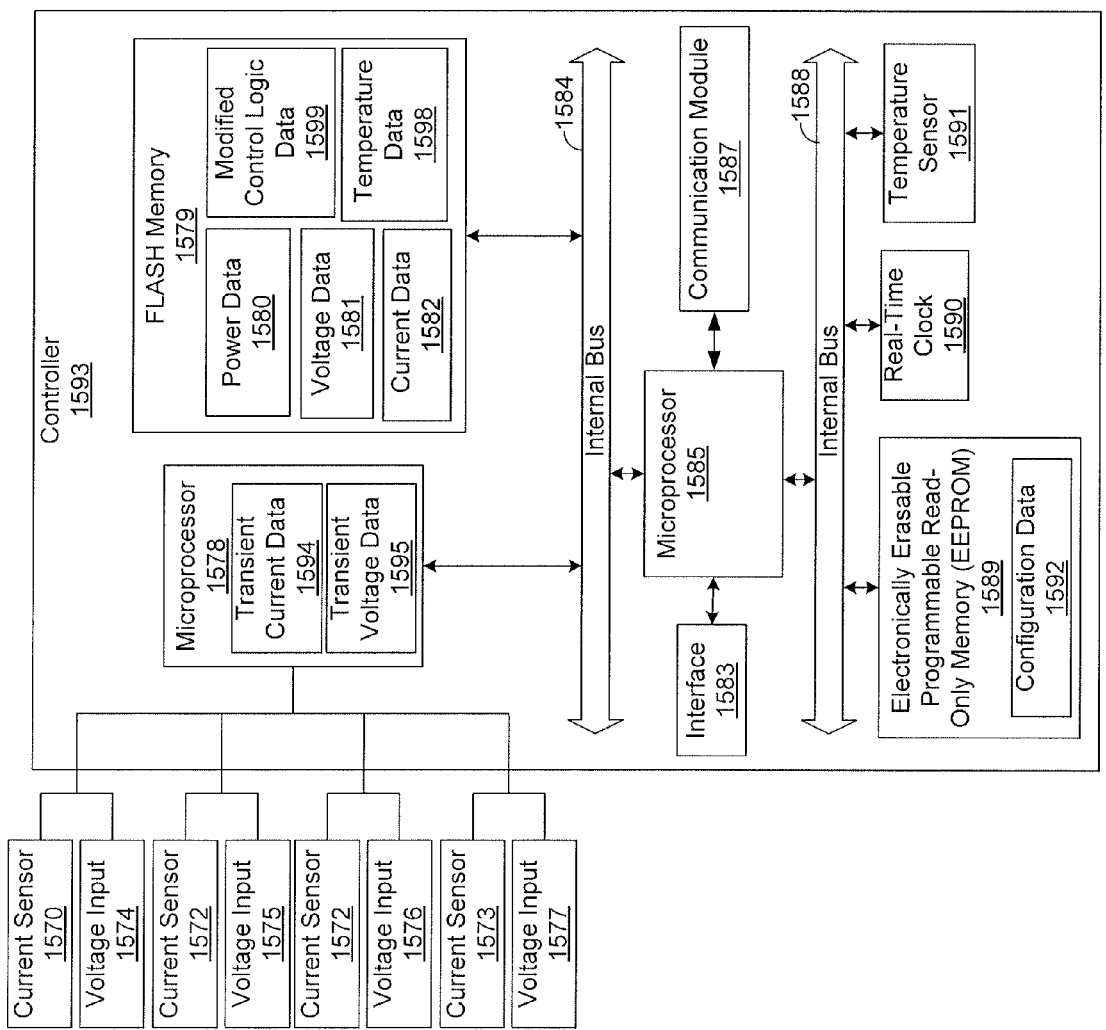
FIG. 15B is a block diagram depicting another exemplary PDTM device, such as is depicted in 14.

FIG. 15B depicts another embodiment of an exemplary controller 1593 that may be housed within the control box 1498 (FIG. 14). As shown by FIG. 15B, the controller 1593 comprises control logic 1586, which behaves similarly to the control logic 1503 (FIG. 15A) shown and described with reference to FIG. 15A. However, in the embodiment depicted in FIG. 15B, the control logic 1586 resides on a microprocessor 1585 that communicates with an internal bus 1584. The control logic 1586 may be software, hardware, or any combination thereof.

In one embodiment, the control logic 1586 is software and is stored in a memory module (not shown) on the microprocessor 1585. In such an embodiment, the control logic 1586 may be designed and written on a separate computing device (not shown) and loaded into the memory module on the microprocessor 1585.

Additionally, the controller 1593 comprises a microprocessor 1578 and FLASH memory 1579 that communicate with the microprocessor 1585 over the internal bus 1584. Further, the controller 1593 comprises an input/output interface 1583 and a communication module 1587 that each communicates with the microprocessor 1585 directly. Note that the interface 1583 and the communication module 1587 may communicate with the microprocessor 1585 indirectly, e.g., vie the buses 1584 or 1585, in other embodiments.

The microprocessor 1578 is electrically coupled to four current sensors 1570-1573 and four voltage inputs 1574-1577. Note that with reference to FIG. 14, such current sensors 1570-1573 and voltage inputs 1574-1577 correlate with satellite units 1490-1493 and voltage leads 1476-1479, respectively.

While four current sensors 1570-1573 and respective voltage inputs 1574-1577 are depicted in FIG. 15B, there can be additional or fewer current sensors 1570-1573 and respective voltage inputs 1574-1577 used in other embodiments. In this regard, the controller 1593 may be used to gather information related to a single phase or two-phase power using device, e.g., a transformer, in other embodiments.

Note that the communication module 1587 is any type of communication module known in the art or future-developed. The communication module 1587 receives data from the microprocessor 1585 and transmits the received data to another computing device. For example, with reference to FIG. 2A, the communication module 1587 may be communicatively coupled to the operations computing device 287 (FIG. 2A) and transmit the data 1594 and 1595 to the operations computing device 187. In one embodiment, the communication module 187 may be wirelessly coupled to the operations computing device 287; however, other types of communication are possible in other embodiments.

The controller 1593 further has electronically erasable programmable read-only memory (EEPROM) 1589, a real-time clock 1590, and a temperature sensor 1591. The EEPROM 1589, the clock 1590, and the sensor 1591 communicate with the microprocessor 1585 via another internal bus 1588.

Note that as shown in the embodiment of the controller 1593, the controller 1593 may comprise two separately accessible internal buses, e.g., buses 1584 and 1588. However, additional or fewer internal buses are possible in other embodiments.

During operation, the microprocessor 1578 receives signals indicative of current and voltage from current sensors 1570-1573 and voltage inputs 1574-1577, respectively. When received, the signals are analog signals. The microprocessor 1578 receives the analog signals, conditions the analog signals, e.g., through filtering, and converts the analog signals indicative of current and voltage measurements into transient current data 1594 and transient voltage data 1595. The microprocessor transmits the data 1594 and 1595 to the microprocessor 1585, and the control logic 1586 stores the data 1594 and 1595 as current data 1582 and voltage data 1581, respectively, in the FLASH memory 1579. Note that while FLASH memory 1579 is shown, other types of memory may be used in other embodiments.

The control logic 1586 may further compute power usage based upon the data 1594 and 1595 received from the microprocessor 1578. In this regard, the control logic may store the power computations in the FLASH memory 1579 as power data 1580.

Further, during operation, the control logic 1586 may receive real-time time stamps associated with a subset of the digital data 1594 and 1595 received from the microprocessor 1578. In such an embodiment, in addition to data indicative of the current and voltage readings taken by the current sensors 1570-1573 and the voltage inputs 1574-1577, the control logic 1586 may also store associated with the current and voltage data indicative of the time that the reading of the associated current and/or voltage was obtained. Thus the FLASH memory 1579 may store historical data for a particular given time period.

During operation, a user (not shown) may desire to load an updated version or modified version of the control logic 1586 onto the microprocessor 1585. In this scenario, the user may transmit data (not shown) indicative of a modified version of the control logic 1586 via the communication module 1587. Upon receipt by the control logic 1586, the control logic 1586 may store data 1599 indicative of the modified version in the FLASH memory 1579. The microprocessor 1585 may then replace the control logic 1586 with the modified control logic data 1599 and continue operation executing the modified control logic data 1599.

The EEPROM 1589 stores configuration data 1592. The configuration data 1592 is any type of data that may be used by the control logic 1586 during operation. For example, the configuration data 1592 may store data indicative of scale factors for use in calibration of the controller 1592, offset, or other calibration data. The configuration data 1592 may be stored in the EEPROM 1589 at manufacturing. In other embodiments, the configuration data 1592 may be updated via the communication module 1587 or the interface 1583, as described hereinafter.

Additionally, the input/output interface 1583 may be, for example, an optical port that connects to a computing device (not shown) or other terminal for interrogation of the controller 1593. In such an embodiment, logic (not shown) on the computing device may request data, e.g., power data 1580, voltage data 1581, current data 1582, or configuration data 1592, via the interface 1583, and in response, the control logic 1586 may transmit data indicative of the data 1580-1582 or 1592 via the interface 1583 to the computing device.

Further, the temperature sensor 1592 collects data indicative of a temperature of the environment in which the sensor resides. For example, the temperature sensor 1592 may obtain temperature measurements within the housing 1498 (FIG. 14). The control logic 1586 receives data indicative of the temperature readings and stores the data as temperature data 1598 in FLASH memory 1579. As described hereinabove with reference to time stamp data, the temperature data 1598 may also be correlated with particular voltage data 1581 and/or current data 1582.

Figure 18:
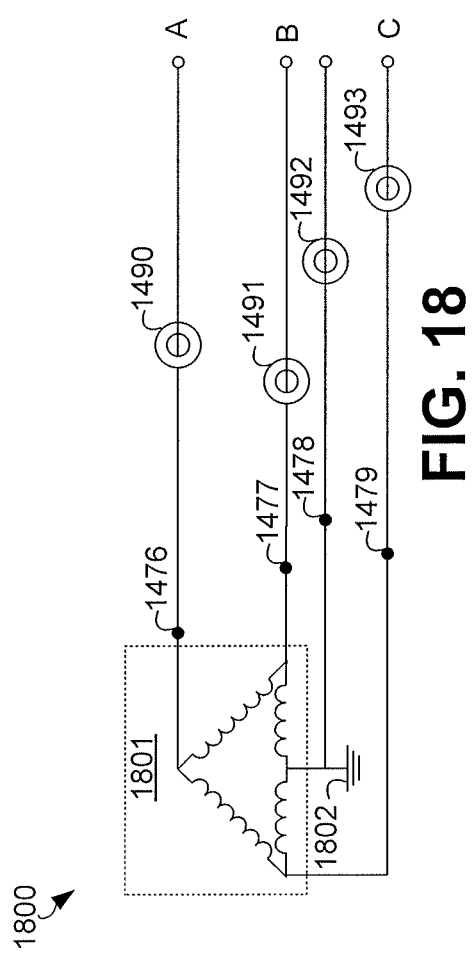
FIG. 18 is a diagram depicting a method of monitoring power with a PDTM of FIG. 14 in accordance with the system such as is depicted in FIG. 1 for a Delta transformer configuration having a center-tapped leg.

FIGS. 16-18 depict exemplary installations on differing types of electrical service connections for three-phase electric power installations. In this regard, FIG. 16 depicts a four-wire grounded "Wye" installation 1600, FIG. 17 depicts a three-wire Delta installation 1700, and FIG. 18 depicts a four-wire tapped Delta neutral grounded installation 1800. Each of these is discussed separately in the contact of installing and operating a PDTM 1499 for the collection of voltage and current data for the calculation of power usage date on the secondary windings (shown per FIGS. 16-18) for each type of installation.

In particular, FIG. 16 is a diagram depicting a Wye installation 1600 (also referred to as a "star" three-phase configuration. While the Wye installation can be a three-wire configuration, the installation 1600 is implemented as a four-wire configuration. The installation comprises the secondary windings of a transformer, which are designated generally as 1601. The installation comprises four conductors, including conductors A, B, C, and N (or neutral), where N is connected to ground 1602. In the installation 1600, the magnitudes of the voltages between each phase conductor (e.g., A, B, and C) are equal. However, the Wye configuration that includes a neutral also provides a second voltage magnitude, which is between each phase and neutral, e.g., 208/120V systems.

During operation, the PDTM 1499 (FIG. 14) is connected to the installation 1600 as indicated. In this regard, satellite current sensor 1490 is coupled about conductor A, and its corresponding voltage ring terminal 1476 is electrically coupled to conductor A. Thus, the control logic 1503 receives data indicative of voltage and current measured from conductor A and stores the corresponding data as voltage data 1501 and current data 1502. Similarly, satellite current sensor 1491 is coupled about conductor B, and its corresponding voltage ring terminal 1477 is electrically coupled to conductor B, satellite current sensor 1492 is coupled about N (neutral), and its corresponding voltage ring terminal 1478 is electrically coupled to N, and, satellite current sensor 1493 is coupled about conductor C, and its corresponding voltage ring terminal 1479 is electrically coupled to conductor C. Thus, over time the control logic 1503 receives and collects data indicative of voltage and current measured from each conductor and neutral and stores the corresponding data as voltage data 1501 and current data 1502. The control logic 1503 may then use the collected data to calculate power usage over the period of time for which voltage and current data is received and collected.

Further, FIG. 17 is a diagram depicting a Delta installation 1700. The Delta installation 1700 shown is a three-wire configuration. The connections made in the Delta configuration are across each of the three phases, or the three secondary windings of the transformer. The installation comprises the secondary windings of a transformer, which are designated generally as 1701. The installation comprises three conductors (i.e., three-wire), including conductors A, B, and C. In the installation 1700, the magnitudes of the voltages between each phase conductor (e.g., A, B, and C) are equal.

During operation, the PDTM 1499 (FIG. 14) is connected to the installation 1700 as indicated. In this regard, satellite current sensor 1490 is coupled about conductor A, and its corresponding voltage ring terminal 1476 is electrically coupled to conductor A. Thus, the control logic 1503 receives data indicative of voltage and current measured from conductor A and stores the corresponding data as voltage data 1501 and current data 1502. Similarly, satellite current sensor 1491 is coupled about conductor B, and its corresponding voltage ring terminal 1477 is electrically coupled to conductor B, and satellite current sensor 1492 is coupled about C, and its corresponding voltage ring terminal 1478 is electrically coupled to C. In regards to the fourth satellite current sensor 1492, because the installation 1700 is a three-wire set up, the fourth satellite current sensor 1493 is not needed, and may therefore not be coupled to a conductor. Similar to the installation 1600, over time the control logic 1503 receives and collects data indicative of voltage and current measured from each conductor (A, B, and C) and stores the corresponding data as voltage data 1501 and current data 1502. The control logic 1503 may then use the collected data to calculate power usage over the period of time for which voltage and current data is received and collected.

FIG. 18 is a diagram depicting a Delta installation 1800 in which one winding is center-tapped to ground 1802, which is often times referred to as a "high-leg Delta configuration." The Delta installation 1800 shown is a four-wire configuration. The connections made in the Delta installation 1800 are across each of the three phases and neutral (or ground), or the three secondary windings of the transformer and ground. The installation 1800 comprises the secondary windings of a transformer, which are designated generally as 1801. The installation comprises three conductors, including conductors A, B, and C and the center-tapped N (neural) wire. The installation 1800 shown is not symmetrical and produces three available voltages.

During operation, the PDTM 1499 (FIG. 14) is connected to the installation 1800 as indicated. In this regard, satellite current sensor 1490 is coupled about conductor A, and its corresponding voltage ring terminal 1476 is electrically coupled to conductor A. Thus, the control logic 1503 receives data indicative of voltage and current measured from conductor A and stores the corresponding data as voltage data 1501 and current data 1502. Similarly, satellite current sensor 1491 is coupled about conductor B, and its corresponding voltage ring terminal 1477 is electrically coupled to conductor B, satellite current sensor 1492 is coupled about N, and its corresponding voltage ring terminal 1478 is electrically coupled to N, and satellite current sensor 1493 is coupled about conductor C, and its corresponding voltage ring terminal 1479 is electrically coupled to C. Similar to the installation 1600, over time the control logic 1503 receives and collects data indicative of voltage and current measured from each conductor (A, B, C, and N) and stores the corresponding data as voltage data 1501 and current data 1502. The control logic 1503 may then use the collected data to calculate power usage over the period of time for which voltage and current data is received and collected.

Figure 19:
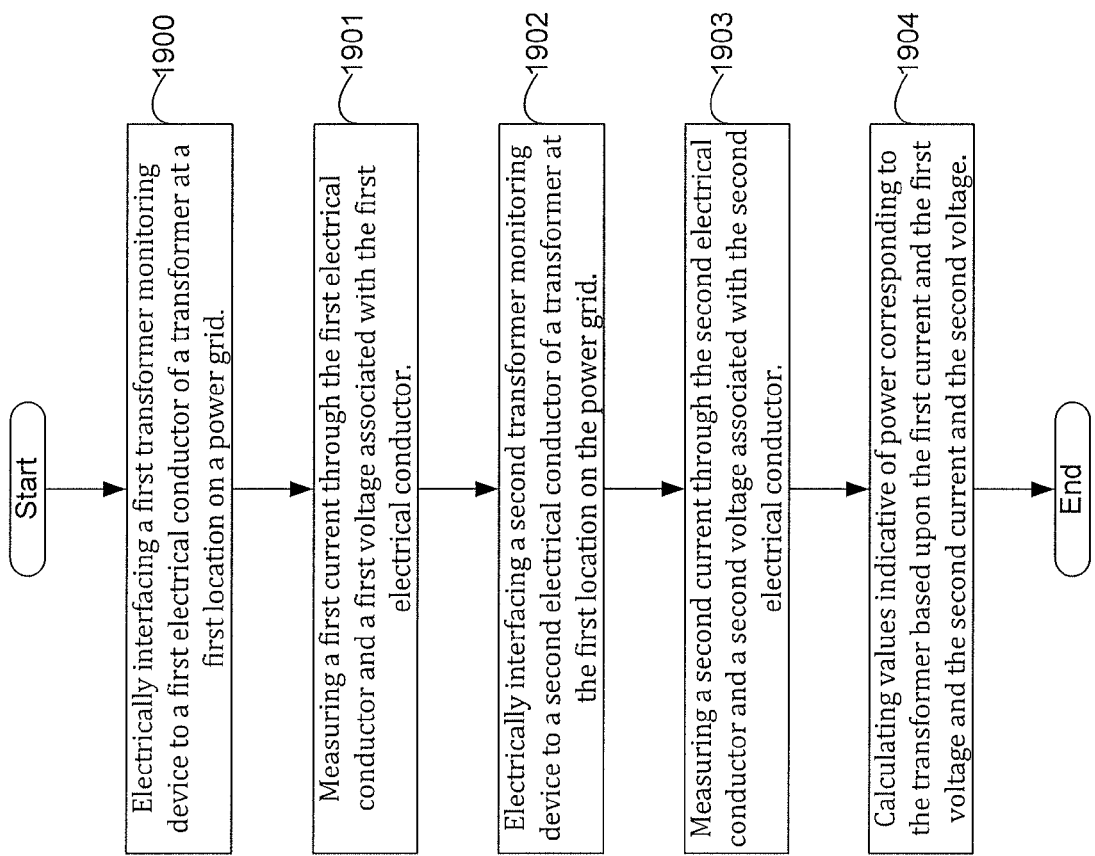
FIG. 19 is a flowchart depicting exemplary architecture and functionality of the power transmission and distribution system such as is depicted in FIG. 1.

FIG. 19 is a flowchart depicting exemplary architecture and functionality of the system 100 depicted in FIG. 1.

In step 1900, electrically interfacing a first transformer monitoring device 1000 (FIG. 3) to a first electrical conductor of a transformer at a first location on a power grid, and in step 1901 measuring a first current through the first electrical conductor and a first voltage associated with the first electrical conductor.

In step 1902, electrically interfacing a second transformer monitoring device 1000 with a second electrical conductor electrically connected to the transformer, and in step 1903 measuring a second current through the second electrical conductor and a second voltage associated with the second electrical conductor.

Finally, in step 1904, calculating values indicative of power corresponding to the transformer based upon the first current and the first voltage and the second current and the second voltage.

Figure 20:
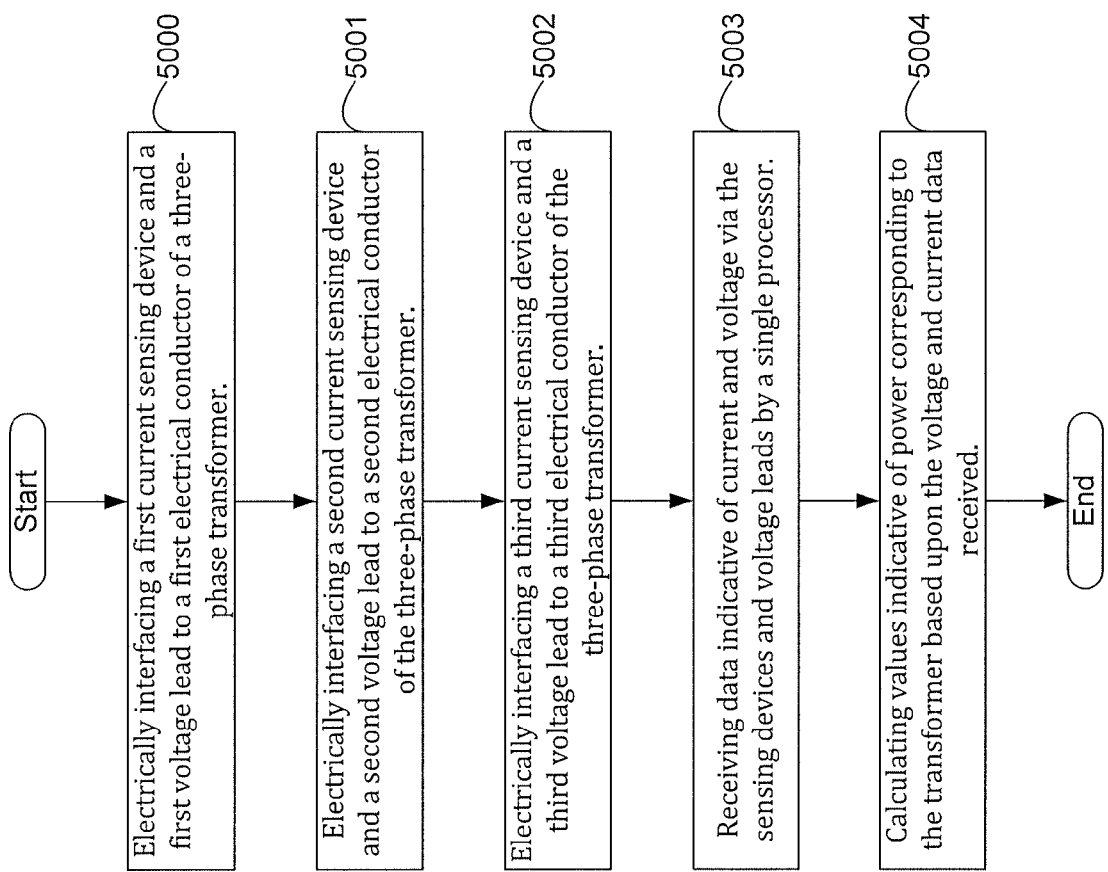
FIG. 20 is a flowchart depicting exemplary architecture and functionality of monitoring the power transmission and distribution system such as is depicted in FIG. 1 with a PDTM of FIG. 14.

FIG. 20 is a flowchart depicting exemplary architecture and functionality of the system 100 depicted in FIG. 1 in regards to the PDTM 1499 (FIG. 14).

In step 5000, electrically interfacing a first current sensing device and a first voltage lead to a first electrical conductor of a three-phase transformer. With reference to FIG. 17, one exemplary installation includes coupling satellite current sensor 1490 to conductor A and ring terminal 1476 to the same conductor A, for example.

In step 5001 electrically interfacing a second current sensing device and a second voltage lead to a second electrical conductor of a three-phase transformer. With reference to FIG. 17, one exemplary installation includes coupling satellite current sensor 1491 to conductor B and ring terminal 1477 to the same conductor B, for example.

In step 5002 electrically interfacing a third current sensing device and a third voltage lead to a third electrical conductor of a three-phase transformer. With reference to FIG. 17, one exemplary installation includes coupling satellite current sensor 1492 to conductor C and ring terminal 1478 to the same conductor C, for example.

In step 5003, receiving data indicative of current and voltage measurements via the sensing devices and the voltage leads by a single processor. Notably, the data is collected over a period of time by the processor 1504 (FIG. 15) and stored in memory 1522 (FIG. 15).

Finally, in step 5004, calculating values indicative of power corresponding to the transformer based upon the voltage and current data received and stored.

What is claimed is:

1. A system for monitoring power, comprising:
a polyphase distribution transformer monitoring (PDTM) device configured to interface with electrical conductors electrically connected to a transformer, the PDTM device further configured to measure a current and a voltage in each of the electrical conductors simultaneously, the PDTM device comprises a plurality of free-moving satellite current sensors, each current sensor undetached from the other current sensors, each satellite current sensor is separately and electrically coupled via a current cable to one of a plurality of connectors on a control box for which to deliver data indicative of current sensed by the current sensors and each current cable is paired with one of a plurality of voltage cables and each current cable and voltage cable pair is coupled to the same connector; and
a processor configured to calculate values indicative of power corresponding to the transformer based upon the currents and the voltages measured and transmit data indicative of the calculated values, the processor further configured to determine a time associated with each current and voltage measured.

2. The system for monitoring power of claim 1, wherein the processor is configured to receive data from each of the current sensors indicative of a sensed current in each of the respective conductors.

3. The system for monitoring power of claim 2, wherein the processor is further configured to received data indicative of voltage of each of the conductors and corresponding to each of the current sensors.

4. The system for monitoring power of claim 1, wherein each connector on the cable box receives one current cable and one voltage cable.

5. The system for monitoring power of claim 4, wherein the control box comprises a current cable interface and a voltage cable interface for each connector.

6. The system of claim 5, wherein the processor is further configured to associate usage data from each of the pairs in memory over time and use the usage data collected over time to calculate power usage for a conductor cable, bus bar, or particular node.

7. The system of claim 1, is shaped as a circle that comprises two separable arches including arch section one and arch section two.

8. The system of claim 7, wherein arch section one is hingedly coupled to arch section two with a hinge.

9. The system of claim 8, wherein when installed and in a closed position, arch section one and arch section two coupled together via a latch and forming a single circle through which a conductor may traverse.

10. The system of claim 9, wherein a coreless current sensor is housed within arch section one and arch section two.

11. A method for monitoring power, comprising:
interfacing a polyphase distribution transformer monitoring (PDTM) device with at least one electrical conductor electrically connected to a transformer, the PDTM device comprising a plurality of free-moving satellite current sensors undetached from the other current sensors;
electrically coupling each separate current sensor via a current cable to one of a plurality of connectors on a control box;
pairing each current cable with one of a plurality of voltage cables;
coupling each current cable and voltage cable pair to the same connector;
measuring a current and a voltage of the electrical conductor via the current sensor and the voltage lead;
calculating values indicative of power corresponding to the transformer based upon the current and the voltage measured;
associating a time stamped with each current and voltage measured; and
transmitting data indicative of the calculated values.

12. The method for monitoring power of claim 11, further comprising electrically coupling at least three current sensors to the control box.

13. The method for monitoring power of claim 12, further comprising receiving data from each of the three current sensors indicative of a sensed current in each of the respective conductors.

14. The method for monitoring power of claim 13, further comprising receiving data indicative of voltage of each of the conductors and corresponding to each of the current sensors.

* * * * *